(12) United States Patent
Choi et al.

(10) Patent No.: US 8,279,705 B2
(45) Date of Patent: Oct. 2, 2012

(54) ULTRASONIC DIAGNOSTIC APPARATUS AND ULTRASONIC TRANSMISSION/RECEPTION METHOD

(75) Inventors: Jaeho Choi, Utsunomiya (JP); Shunji Terasawa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/331,697

(22) Filed: Dec. 20, 2011

(65) Prior Publication Data

US 2012/0099394 A1    Apr. 26, 2012

Related U.S. Application Data

(63) Continuation of application No. PCT/JP2011/072772, filed on Oct. 3, 2011.

(30) Foreign Application Priority Data

Oct. 20, 2010 (JP) ................................. 2010-235313

(51) Int. Cl.
*G03B 42/06* (2006.01)
*A61B 8/00* (2006.01)
(52) U.S. Cl. ................. 367/7; 73/602; 600/447
(58) Field of Classification Search .............. 367/103, 367/119; 600/447; 73/602, 629
See application file for complete search history.

(56) References Cited

U.S. PATENT DOCUMENTS

| 5,544,128 | A | * | 8/1996 | Kim et al. | ...................... 367/119 |
| 5,566,675 | A | * | 10/1996 | Li et al. | ........................... 600/459 |
| 5,997,479 | A | * | 12/1999 | Savord et al. | ................. 600/447 |
| 6,638,226 | B2 | * | 10/2003 | He et al. | ........................ 600/443 |
| 6,856,577 | B1 | * | 2/2005 | Handa et al. | ................... 367/119 |
| 2008/0154133 | A1 | | 6/2008 | Shiki | |

FOREIGN PATENT DOCUMENTS

| JP | 10-118063 | 5/1998 |
| JP | 2831719 | 9/1998 |
| JP | 11-221217 | 8/1999 |
| JP | 2008-73085 | 4/2008 |

OTHER PUBLICATIONS

International Search Report and Written Opinion issued Dec. 27, 2011 in Patent Application No. PCT/JP2011/072772 with English Translation of Category of Cited Documents.

* cited by examiner

*Primary Examiner* — Ian Lobo

(74) *Attorney, Agent, or Firm* — Oblon, Spivak, McClelland, Maier & Neustadt, L.L.P.

(57) ABSTRACT

According to one embodiment, a reception unit generates reception beam data set groups based on echo signals. Each of the reception beam data set groups includes reception beam data sets respectively corresponding to reception beams associated with parallel signal processing. Each of the reception beam data sets is generated based on echo signals from transducers associated with a corresponding reception position. A scanning control unit sets the spatial arrangement of the reception beams. The reception beams are arranged at unequal intervals. A synthesizing unit generates synthetic beam data sets associated with reception positions based on the reception beam data set groups. Each of the synthetic beam data sets is obtained by synthesizing reception beam data sets associated with the same reception position. An image generation unit generates ultrasonic image data based on the synthetic beam data sets.

16 Claims, 17 Drawing Sheets

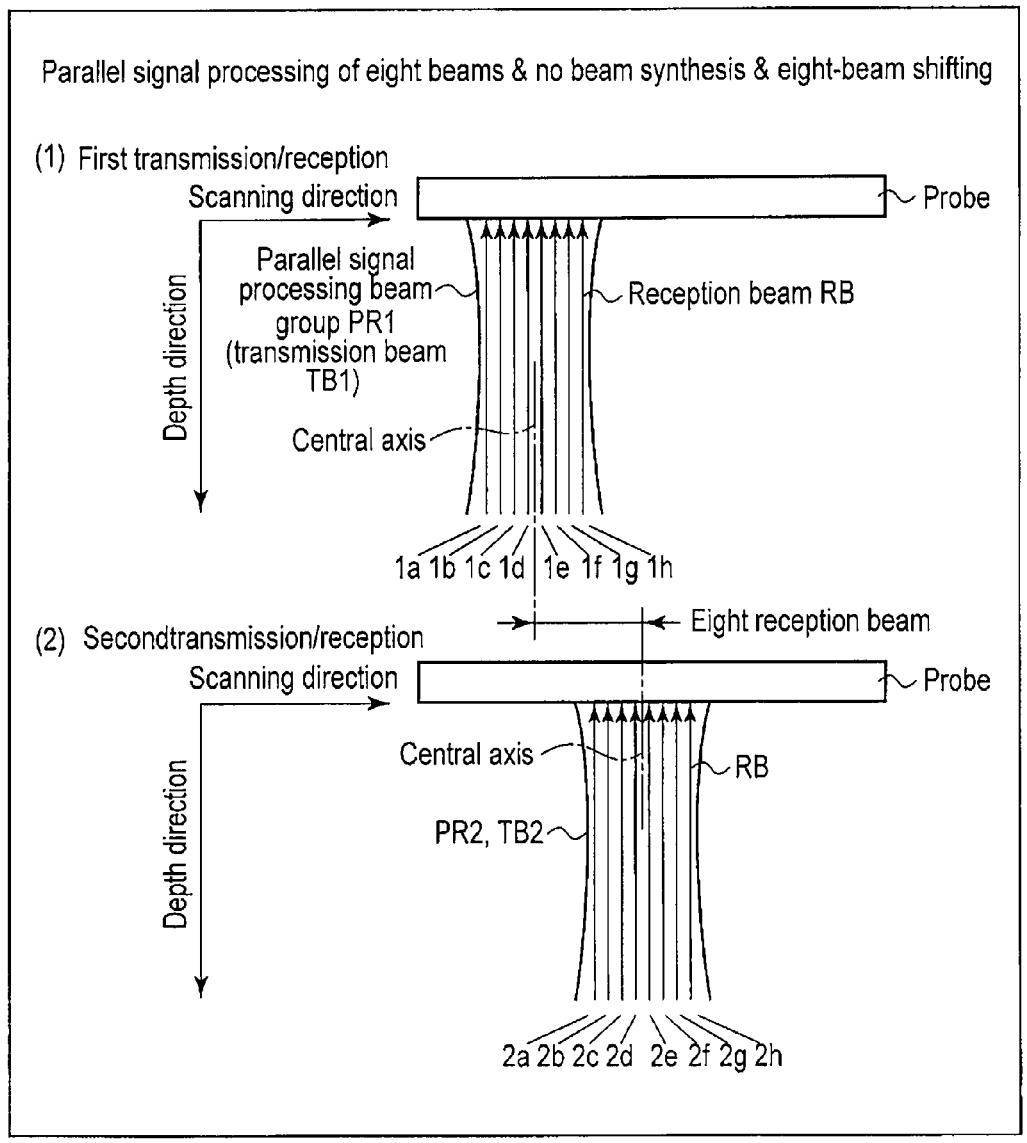
F I G. 11

ULTRASONIC DIAGNOSTIC APPARATUS AND ULTRASONIC TRANSMISSION/RECEPTION METHOD

CROSS REFERENCE TO RELATED APPLICATIONS

This application is a Continuation Application of PCT Application No. PCT/JP2011/072772, filed Oct. 3, 2011 and based upon and claiming the benefit of priority from prior Japanese Patent Application No. 2010-235313, filed Oct. 20, 2010, the entire contents of all of which are incorporated herein by reference.

FIELD

Embodiments described herein relate generally to an ultrasonic diagnostic apparatus and an ultrasonic transmission/reception method.

BACKGROUND

A parallel signal processing (PSP) method has been proposed for ultrasonic diagnostic apparatuses to increase a frame rate. In the PSP method, an ultrasonic diagnostic apparatus transmits an ultrasonic transmission beam in a transmission direction. The transmission beam is reflected by a subject. The ultrasonic diagnostic apparatus then receives the reflected ultrasonic waves and generates echo signals corresponding to the received ultrasonic waves. The ultrasonic diagnostic apparatus generates a plurality of reception beam data sets respectively corresponding to a plurality of reception beams based on the generated echo signals. In this manner, in PSP, the ultrasonic diagnostic apparatus simultaneously receives a plurality of reception beams with respect to one transmission of a transmission beam. This increases the amount of data per unit time.

FIG. 11 is a view showing the positions of reception beams in a standard scanning scheme for PSP. The following description will exemplify the simultaneous reception of eight beams. Note that the simultaneous reception of eight beams is a scanning scheme for simultaneously receiving eight reception beams with respect to the transmission of one transmission beam. The abscissa represents the transmission direction of transmission/reception beams; and the ordinate, the depth direction of transmission/reception beams. In this case, eight reception beams to be parallelly and simultaneously received at once will be collectively referred to as a PSP beam group. A plurality of reception beam data sets associated with a PSP beam group will be collectively referred to as a PSP beam data set group. In addition, a series of processing operations from the transmission of one transmission beam to the reception of reception beams will be referred to as one transmission/reception.

Referring to FIG. 11, eight reception beams RB to be parallelly and simultaneously received in the first transmission/reception are represented by the number "1", and the reception beams in a PSP beam group PR are represented by "a", "b", "c", "d", "e", "f", "g", and "h" from the left in the scanning order. As indicated by (1) in FIG. 11, in the first transmission/reception, a transmission beam TB is transmitted. The central axis of the transmission beam TB in the first transmission/reception is located in the middle between "1d" and "1e". The eight reception beams RB indicated by "1a", "1b", "1c", "1d", "1e", "1f", "1g", and "1h" are parallelly and simultaneously received. The eight reception beams RB are arranged at equal intervals in the scanning direction. More specifically, the interval between the center positions of the adjacent reception beams RB (the interval between the central axes) is set to one reception beam. In this case, the position of the central axis of the reception beam RB on a probe will be referred to as a reception position. In other words, a reception position is defined as the center of the reception opening used for the reception of the reception beams RB. As indicated by (2) in FIG. 11, the central axis of a second transmission beam TB2 is located in the middle between "2d" and "2e", which is shifted from the central axis of a first transmission TB1 by eight reception beams in the scanning direction. In the second transmission/reception, eight reception beams represented by "2a", "2b", "2c", "2d", "2e", "2f", "2g", and "2h" are parallelly and simultaneously received. Note that the scanning scheme in which the interval between the central axes of two adjacent PSP beam groups corresponds to eight reception beams is called "8-beam shifting". In this case, two adjacent PSP beam groups PR1 and PR2 do not spatially overlap, and hence beam synthesis (to be described later) is not performed.

In PSP, however, since the position of the central axis of a transmission beam differs from that of each reception beam, the transmission/reception sensitivity deteriorates, and it is impossible to obtain uniform transmission/reception sensitivity.

FIGS. 12 and 13 are views for explaining reception sensitivity nonuniformity in the scanning scheme in FIG. 11. As indicated by (2) in FIG. 12 or (2) in FIG. 13, the sound pressure in the transmission sound field at an end portion of the transmission beam TB in the scanning direction is lower than that at the middle portion. For this reason, if the number of reception beams to be parallelly and simultaneously received is set to three or more, transmission/reception sound fields become nonuniform in magnitude (i.e., reception sensitivity) in the scanning direction. As indicated by (2) in FIG. 12 or (2) in FIG. 13, therefore, the reception beams at the middle portion and end portions of the PSP beam group PR become uneven in reception sensitivity. Unevenness in reception sensitivity will lead to a deterioration in the image quality of an ultrasonic image.

In PSP, the PSP beam group obtained by preceding transmission/reception differs in phase from that obtained by succeeding transmission/reception. FIG. 14 is a view for explaining phase differences between PSP beam groups in the scanning scheme in FIG. 11. As shown in FIG. 14, the phases of reception beams switch every time PSP beam groups switch, that is, for every eight reception beams. In this case, the phases of beams are synonymous with the order (numbers) of beams generated in transmission/reception. For example, a plurality of reception beams in the first transmission/reception all belong to the same phase. The PSP beam group in the first transmission/reception differs in phase from that in the second transmission/reception.

FIG. 15 is a view for explaining the scanning scheme in FIG. 11 (simultaneous reception of eight beams & no beam synthesis & eight-beam shifting). As shown in FIG. 15, in the first transmission/reception, eight reception beams ("1a", "1b", "1c", "1d", "1e", "1f", "1g", and "1h") are received. These eight reception beams constitute a PSP beam group PB1. Subsequently, likewise, PSP beam groups PB2, PB3, and PB4 are respectively received in the second, third, and fourth transmissions/receptions. The respective reception beams are sequentially output (in the reception order) without beam synthesis. Assume that the sensitivity of reception beams at positions "a" and "h" is 7, the sensitivity of reception beams at positions "b" and "g" is 8, the sensitivity of reception beams at positions "c" and "f" is 9, and the sensitivity of reception beams at positions "d" and "e" is 10. As shown in FIG. 15, transmission/reception sensitivity nonuniformity (reception sensitivity unevenness) occurs between the reception beams of each PSP beam group PB in accordance with the distances from the central axis of each PSP beam group. In addition, since adjacent PSP beam groups do not spatially overlap, the phases of output beams (reception beams) switch for each PSP beam group. Such transmission/reception sensitivity nonuniformity and phase differences will produce artifacts in ultrasonic images in a density stripe pattern, resulting in a deterioration in image quality. This deterioration in image quality worsens with an increase in the number of PSP beams.

In order to solve this problem, there have been proposed a transmission delay addition technique and a transmission wavefront synthesizing technique. FIG. 16 is a view showing the positions of reception beams in another scanning scheme for PSP (parallel signal processing of eight beams & eight-beam synthesis & one-beam shifting). FIG. 17 is a view for explaining the scanning scheme in FIG. 16. As shown in FIGS. 16 and 17, the central axis of a first transmission beam TB1 is located in the middle between "1d" and "1e". The central axis of a second transmission beam TB2 is located in the middle between "2d" and "2e" shifted from the central axis of the first transmission beam TB1 by one reception beam in the scanning direction. At this time, for example, reception beams RB respectively indicated by "1h" and "2g" are located at spatially the same reception position. At the end of the eighth transmission/reception, eight reception beams RB belonging to a different PSP beam group (in other words, at different reception times) are obtained. For example, at a reception position PZ, eight reception beams indicated by "1h", "2g", "3f", "4e", "5d", "6c", "7b", and "8a" are obtained. Synthesizing the eight reception beams at spatially the same position will generate a synthetic beam. For example, synthesizing the reception beams indicated by "1h", "2g", "3f", "4e", "5d", "6c", "7b", and "8a" will generate a synthetic beam O1. Repeating transmission/reception while shifting the central axis of the transmission beam TB by one reception beam at a time in this manner will receive eight reception beams at spatially the same position and generate a synthetic beam based on the eight reception beams. This makes the reception sensitivity of an output beam (synthetic beam) after synthesis uniform in the scanning direction. In addition, since reception beams are synthesized as PSP beam groups spatially overlap, the phases of synthetic beams switch for each synthetic beam. It is therefore possible to reduce artifacts in a stripe pattern due to phase differences on a PSP beam group basis.

However, since one synthetic beam is generated by synthesizing a plurality of reception beams, the larger the number of reception beams to be synthesized, the lower the frame rate. In addition, as the number of reception beams to be synthesized increases, the phase differences between the reception beams to be synthesized increase. This makes it difficult to apply this technique to fast moving regions such as the heart.

FIG. 18 is a view for explaining a still another scanning scheme for PSP (parallel signal processing of eight beams & four-beam synthesis & two-beam shifting). The number of reception beams to be synthesized in the scanning scheme in FIG. 18 is decreased from eight to four to increase the frame rate. In this case, it is possible to simultaneously increase the frame rate and reduce artifacts in a stripe pattern due to phase differences on a PSP beam group basis. However, since two reception beams are shifted at a time in the scanning direction, the phases of synthetic beams switch for every two synthetic beams instead of one synthetic beam. This causes image shifts in an ultrasonic image, resulting in an unnatural image.

It is an object of the embodiment to provide an ultrasonic diagnostic apparatus and ultrasonic transmission/reception method which can improve image quality in PSP.

BRIEF DESCRIPTION OF THE DRAWINGS

FIG. 11 is a view showing the positions of reception beams in a standard scanning scheme for PSP (parallel signal processing of eight beams & no beam synthesis & eight-beam shifting).

DETAILED DESCRIPTION

In general, according to one embodiment, an ultrasonic diagnostic apparatus according to this embodiment includes a probe, a reception unit, a control unit, a synthesizing unit, and a generation unit. The probe includes a plurality of transducers configured to repeatedly transmit transmission beams to a subject, repeatedly receive ultrasonic waves reflected by the subject, and repeatedly generate echo signals corresponding to the received ultrasonic waves. The reception unit generates a plurality of reception beam data set groups based on the generated echo signals. Each of the reception beam data set groups includes a plurality of reception beam data sets respectively corresponding to a plurality of reception beams associated with PSP. Each of the reception beam data sets is generated based on echo signals from transducers, of the transducers, which are associated with a corresponding reception position. The control unit sets a spatial arrangement of the reception beams and arranges the reception beams at unequal intervals. The synthesizing unit generates a plurality of synthetic beam data sets associated with a plurality of reception positions based on the reception beam data set groups. Each of the synthetic beam data sets is obtained by synthesizing reception beam data sets, of the reception beam data sets included in the reception beam data set groups, which are associated with the same reception position. The generation unit generates ultrasonic image data associated with the subject based on the synthetic beam data sets.

An ultrasonic diagnostic apparatus and ultrasonic transmission/reception method according to an embodiment will be described below with reference to the accompanying drawings.

Figure 1:
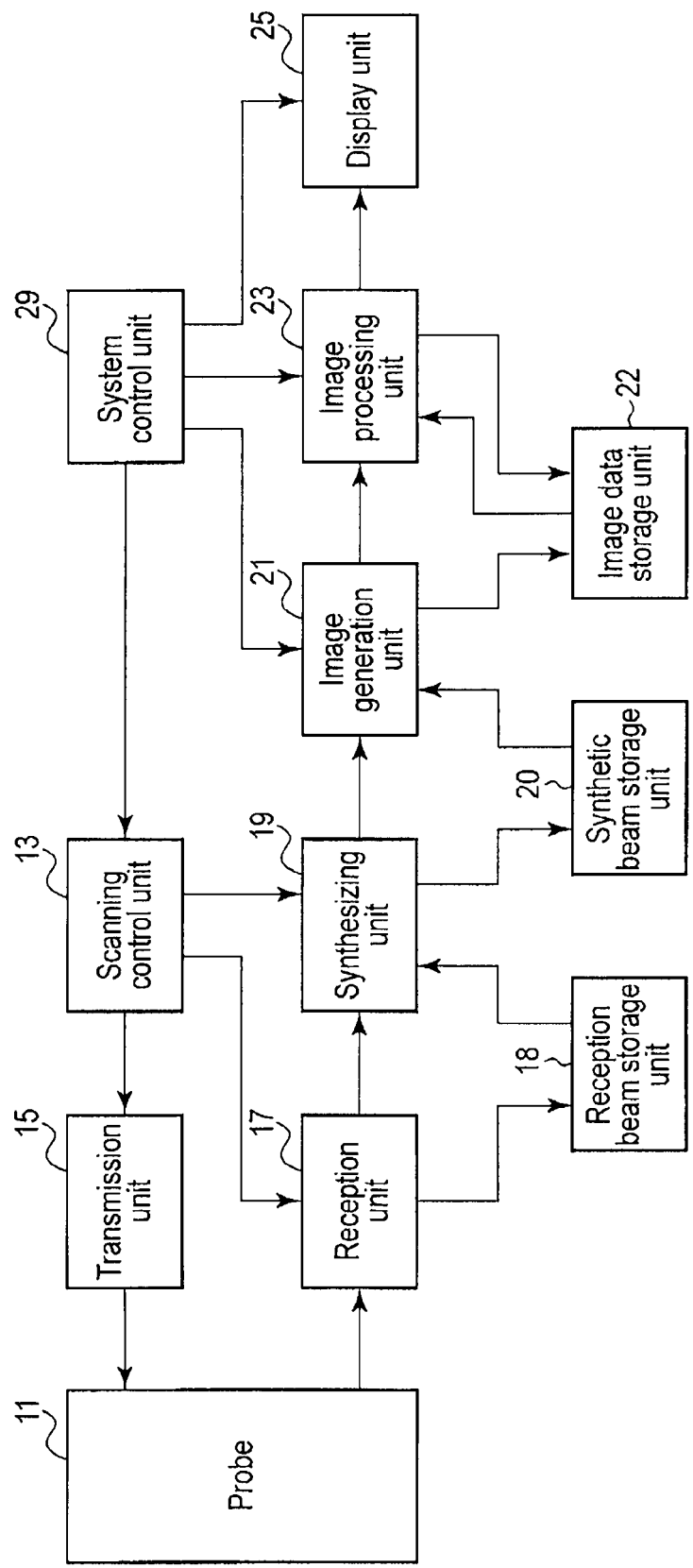
FIG. 1 is a block diagram showing the arrangement of an ultrasonic diagnostic apparatus according to an embodiment.

FIG. 1 is a block diagram showing the arrangement of an ultrasonic diagnostic apparatus according to this embodiment. As shown in FIG. 1, the ultrasonic diagnostic apparatus according to the embodiment includes a probe 11, a scanning control unit 13, a transmission unit 15, a reception unit 17, a reception beam storage unit 18, a synthesizing unit 19, a synthetic beam storage unit 20, an image generation unit 21, an image data storage unit 22, an image processing unit 23, a display unit 25, and a system control unit 29.

The probe 11 is of an electronic scanning type. The probe 11 includes a plurality of transducers arrayed two-dimensionally. Each transducer receives a driving pulse from the transmission unit 15 and transmits an ultrasonic wave to a subject. The ultrasonic waves are sequentially reflected by the discontinuity points of acoustic impedance of an internal body tissue. The transducers receive the reflected ultrasonic waves. The transducers generate echo signals corresponding to the intensities of received ultrasonic waves. An echo signal is an analog electrical signal. The ultrasonic waves generated from a plurality of transducers form a transmission beam to be transmitted to the transmission position determined in accordance with the supply timing of a driving pulse from the transmission unit 15 to each transducer. In this manner, the probe 11 repeatedly transmits a transmission beam to a subject, repeatedly receives ultrasonic waves reflected by the subject, and repeatedly generates echo signals corresponding to the received ultrasonic waves. The generated echo signals are supplied to the reception unit 17.

The scanning control unit 13 determines scanning conditions in accordance with an instruction from the system control unit 29. Instructions from the system control unit 29 include a frame rate, the number of frames, and the number of beams. An instruction from the system control unit 29 may be an operator's instruction associated with scanning conditions input via an input unit (not shown). The scanning conditions include, for example, a PRF (Pulse Repetition Frequency), a transmission position, reception positions (the spatial positions of reception beams), a reception opening, the intervals between the central axes of PSP beam groups (the number of beams to be shifted), void positions, void widths, and synthesizing information. Note that a beam position is defined as the position of the central axis of a beam relative to the probe 11. The scanning control unit 13 controls the transmission unit 15, the reception unit 17, and the synthesizing unit 19 in accordance with these scanning conditions. Assume that the scanning control unit 13 according to this embodiment executes B-mode scanning.

The transmission unit 15 supplies driving pulses to the probe 11 in accordance with scanning conditions from the scanning control unit 13 so as to make the probe 11 transmit a transmission beam to a desired transmission position. More specifically, the transmission unit 15 repeatedly generates a rate pulse for each channel in accordance with the preset PRF. The transmission unit 15 gives each rate pulse a delay time necessary to form a transmission beam associated with a preset transmission position. This delay time is determined, for example, for each transducer in accordance with a transmission position. The transmission unit 15 generates a driving pulse at the timing based on each delayed rate pulse, and supplies the generated driving pulse to each transducer. Upon receiving the driving pulse, each transducer generates an ultrasonic wave. With this operation, the probe 11 transmits a transmission beam to the preset transmission position.

The reception unit 17 executes PSP processing for echo signals from the probe 11 in accordance with scanning conditions from the scanning control unit 13, and generates a plurality of PSP beam data set groups corresponding to a plurality of PSP beam groups having different center positions. Note that the center position of a PSP beam group is defined to the position of the central axis of the PSP beam group relative to the probe 11. One PSP beam group includes a plurality of reception beams. Typically, the central axis of a PSP beam group is matched with the central axis of a corresponding transmission beam. That is, the reception unit 17 generates a plurality of reception beam data sets respectively corresponding to a plurality of reception beams with respect to each PSP beam group. The reception unit 17 instantly supplies the generated reception beam data sets to the reception beam storage unit 18 or the synthesizing unit 19. The arrangement of the respective reception beams in the PSP beam group will be described later.

A method of generating reception beam data sets will be described in detail later. The reception unit 17 receives an echo signal from each transducer of the probe 11, amplifies the received echo signal, and analog/digital-converts the amplified echo signal. The reception unit 17 then stores the digitally converted echo signal in a digital memory. For example, a digital memory is provided for each transducer. The echo signal is stored at an address corresponding to the reception time of the echo signal in the digital memory corresponding to the transducer from which the signal is received. The reception unit 17 generates a reception beam data set corresponding to a reception beam data set corresponding to the reception beams associated with the reception positions by reading out echo signals from the addresses corresponding to the preset reception positions and adding the signals. The generated reception beam data set is instantly supplied to the reception beam storage unit 18 or the synthesizing unit 19. Note that "to generate a reception signal corresponding to a reception beam" is synonymous with "to receive a reception beam". A set of a plurality of transducers used for the reception of one reception beam is called a reception opening.

Figure 2:
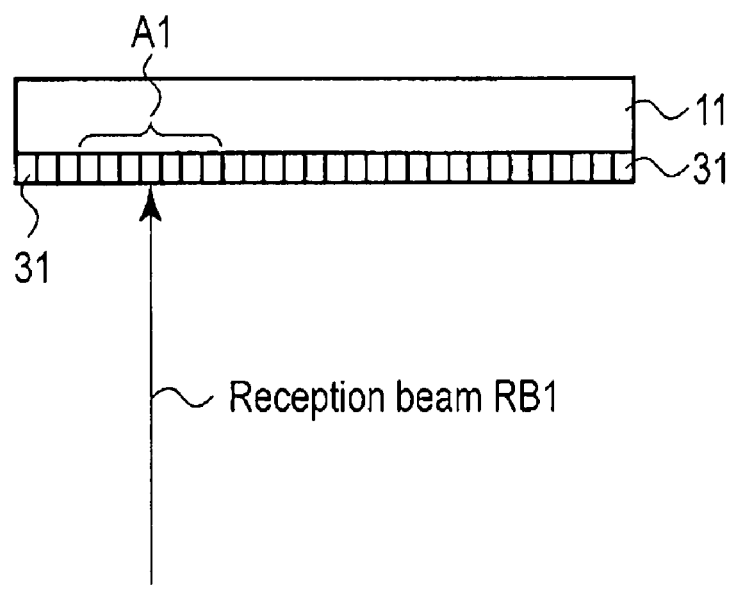
FIG. 2 is a view for explaining a reception opening according to this embodiment.
Figure 3:
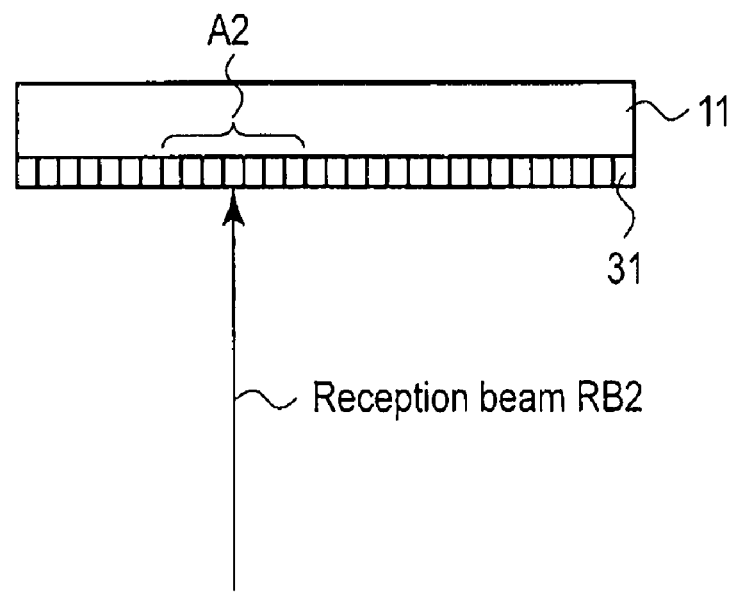
FIG. 3 is another view for explaining a reception opening according to this embodiment.

FIGS. 2 and 3 are views for explaining a reception opening A. As shown in FIGS. 2 and 3, a set of a plurality of transducers 31 used for the reception of one reception beam RB constitute the reception opening A. For example, as shown in FIG. 2, a reception opening A1 is used for the reception of a reception beam RB1. As shown in FIG. 3, a reception opening A2 at a position different from that of the reception opening A1 is used for the reception of a reception beam RB2. In this manner, the reception unit 17 receives a plurality of reception beams RB in one transmission/reception while moving the reception opening A along the scanning direction. In other words, the reception unit 17 generates a reception beam data set associated with the reception beam RB to be received based on echo signals from the transducers 31 constituting the reception opening A corresponding to the reception beam RB to be received. Typically, the number of transducers 31 constituting the reception opening A is not changed in accordance with the position of the reception opening A but is fixed. The number of transducers constituting the reception opening A is smaller than the number of transducers included in the probe 11. Note that it is possible to arbitrarily set the number of transducers constituting the reception opening A.

The reception beam storage unit 18 stores reception beam data from the reception unit 17. The reception beam data is stored in association with, for example, a reception position and a transmission/reception number. Note that the transmission/reception number is defined as the number of times of transmission/reception from the start time of ultrasonic scanning.

The synthesizing unit 19 performs synthesizing processing for reception beam data sets from the reception unit 17 or the reception beam storage unit 18 to generate a synthetic beam data set associated with a synthetic beam in accordance with scanning conditions from the scanning control unit 13. More specifically, based on a plurality of reception beam data sets associated with the same reception position, the synthesizing unit 19 generates a synthetic beam data set associated with the reception position. The synthesizing unit 19 instantly supplies the generated synthetic beam data set to the synthetic beam storage unit 20 or the image generation unit 21.

The synthetic beam storage unit 20 stores a synthetic beam data set from the synthesizing unit 19. The synthetic beam data set is stored in association with an output time from the synthesizing unit 19 and a spatial position. Typically, the synthetic beam storage unit 20 stores synthetic beam data sets at storage addresses corresponding to an output order from the synthesizing unit 19.

The image generation unit 21 generates ultrasonic image data associated with a subject based on a synthetic beam data set from the synthesizing unit 19 or the synthetic beam storage unit 20 under the control of the system control unit 29. The generated ultrasonic image data is instantly supplied to the image data storage unit 22 and the image processing unit 23.

The image data storage unit 22 stores ultrasonic image data from the image generation unit 21 and ultrasonic image data from the image processing unit 23.

The image processing unit 23 performs image processing such as filter processing for ultrasonic image data from the image generation unit 21 or the image data storage unit 22 under the control of the system control unit 29. The ultrasonic image data having undergone the image processing is supplied to the image data storage unit 22 and the display unit 25.

The display unit 25 displays an ultrasonic image corresponding to the ultrasonic image data from the image processing unit 23 under the control of the system control unit 29.

The system control unit 29 functions as the main unit of the ultrasonic diagnostic apparatus. The system control unit 29 expands a dedicated program for ultrasonic examination according to this embodiment, controls the respective units in accordance with instructions indicated by the dedicated program, and executes ultrasonic examination according to the embodiment.

Ultrasonic examination to be performed under the control of the system control unit 29 will be described in detail below. Ultrasonic examination according to this embodiment features the arrangement of reception beams included in a PSP beam group.

The scanning control unit 13 sets the spatial arrangement of reception beams in accordance with the above scanning conditions. More specifically, the scanning control unit 13 arranges a plurality of reception beams of each PSP beam group at unequal intervals.

Figure 4:
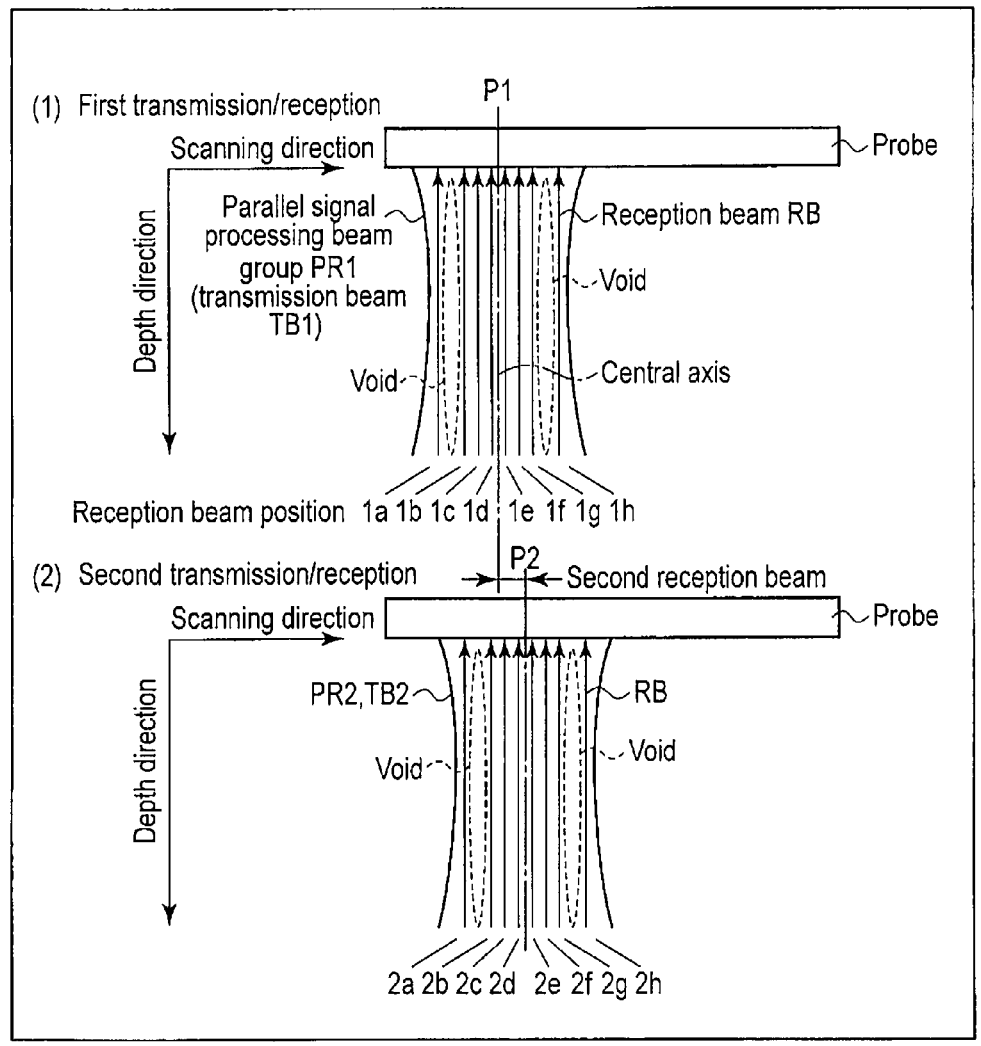
FIG. 4 is a view showing an example of the arrangement of reception beams included in a PSP beam group received by a reception unit in FIG. 1.
Figure 5:
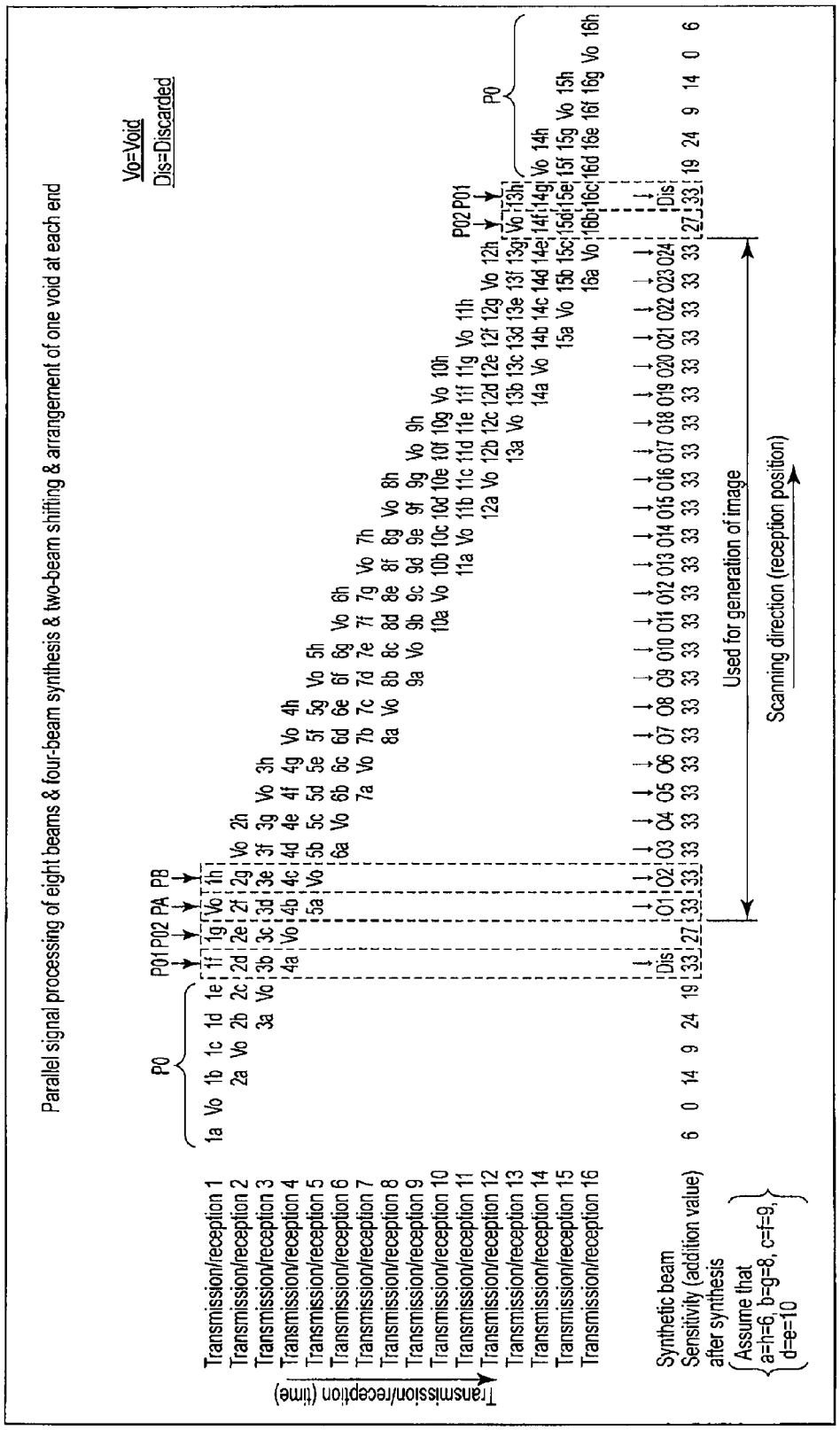
FIG. 5 is a view for explaining a scanning scheme for PSP (parallel signal processing of eight beams & four-beam synthesis & two-beam shifting & arrangement of one void at each end) with the arrangement of reception beams in FIG. 4.

FIG. 4 is a view showing an example of the arrangement of reception beams included in a PSP beam group. FIG. 5 is a view for explaining the scanning scheme for PSP in the case of the reception beam arrangement shown in FIG. 4. For the sake of a concrete description, assume that the number of PSP beams is eight. Note that the number of PSP beams in this embodiment is not limited to eight, and may be set to an arbitrary number equal to or more than three. In addition, assume that the number of beams to be shifted is two. However, the number of beams to be shifted in the embodiment is not limited to two, and may be set to an arbitrary number equal to or more than two.

As shown in FIGS. 4 and 5, each PSP beam group PR includes a plurality of reception beams RB. The reception beams RB correspond to different reception openings. The intervals between the center positions of the adjacent reception beams RB are set to unequal intervals. Note that the intervals between the center positions are defined as the intervals between the central axes of the adjacent reception beams RB in the scanning direction. In other words, the intervals between the center positions are defined as the intervals between the centers of the adjacent reception openings in the scanning direction. The intervals between center positions will be referred to as the intervals between central axes hereinafter. The intervals between the central axes of the adjacent reception beams RB include the first and second intervals.

Figure 15:
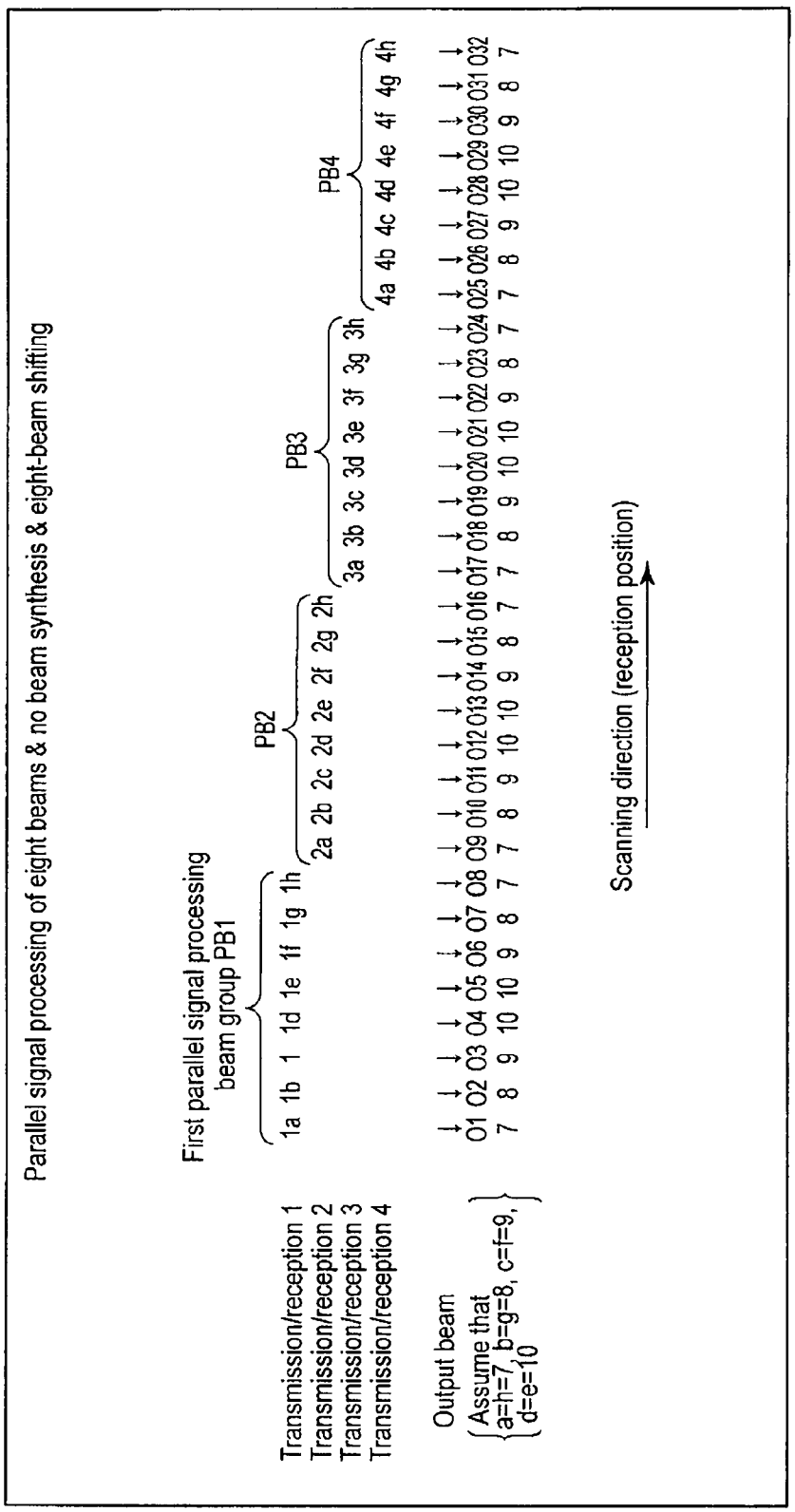
FIG. 15 is a view for explaining the scanning scheme in FIG. 11.
Figure 16:
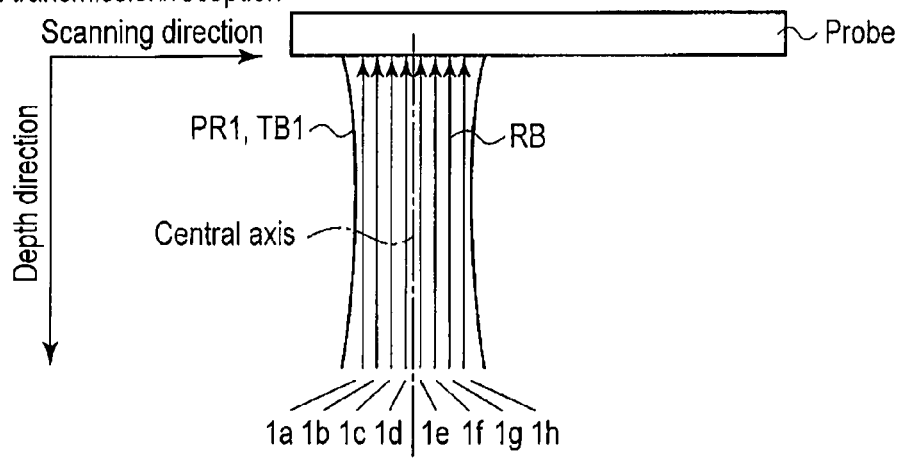
FIG. 16 is a view showing the positions of reception beams in another scanning scheme for PSP (parallel signal processing of eight beams & eight-beam synthesis & one-beam shifting).
Figure 16:
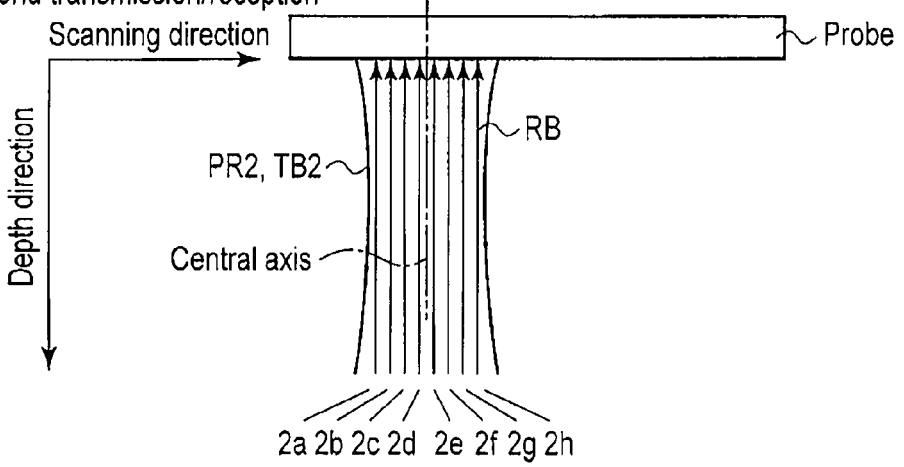
Figure 17:
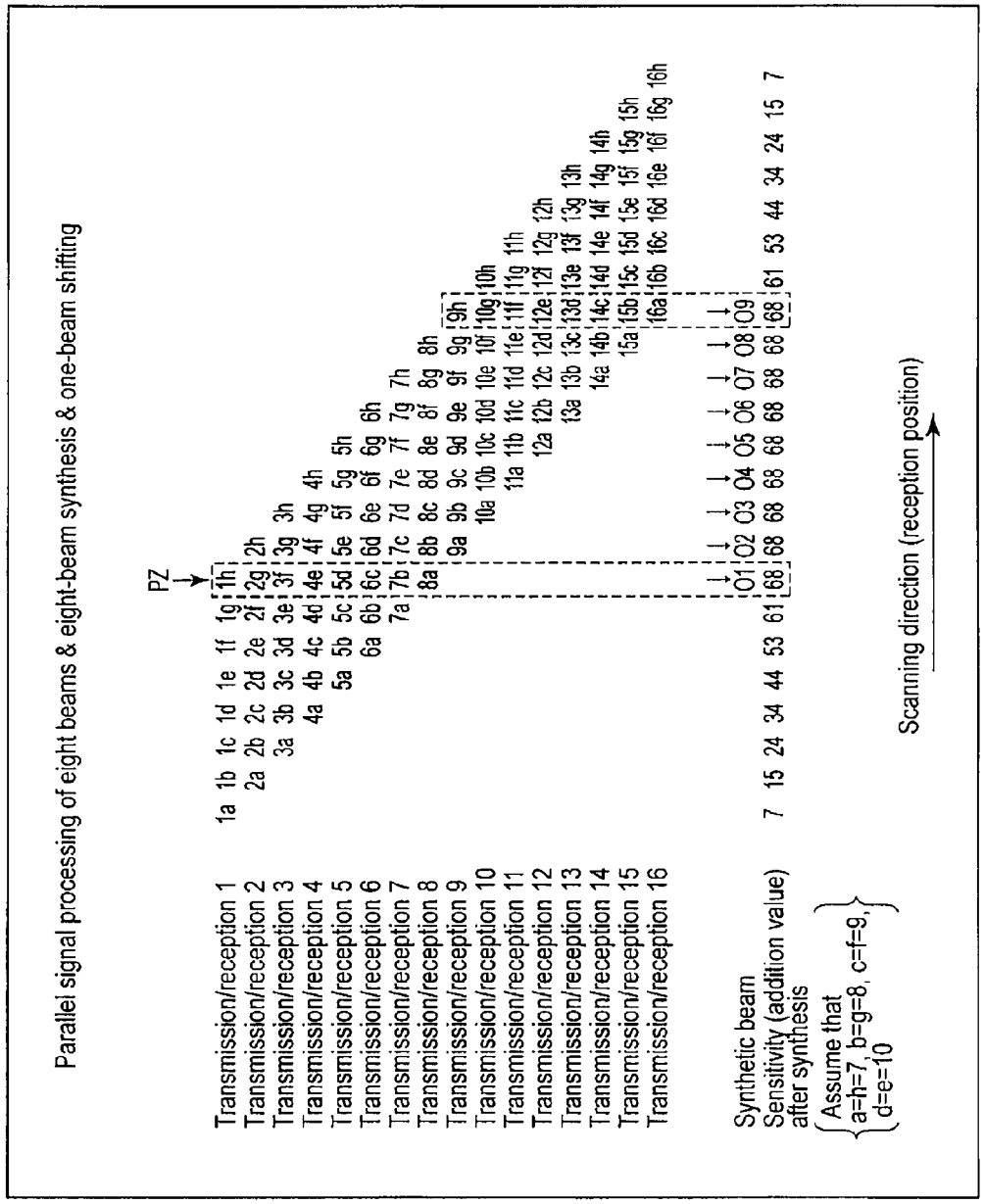
FIG. 17 is a view for explaining the scanning scheme in FIG. 16.

The first interval is set to the width of one reception beam RB. In other words, the first interval is the interval between the central axes of two adjacent reception beams which are spatially continuous along the scanning direction. As shown in FIGS. 4 and 5, the following intervals are set to the first interval: the interval between the reception beams RB respectively indicated by "b" and "c", the interval between the reception beams RB respectively indicated by "c" and "d", the interval between the reception beams RB respectively indicated by "d" and "e", the interval between the reception beams RB respectively indicated by "e" and "f", and the interval between the reception beams RB respectively indicated by "f" and "g". The first interval is equal to the interval between the central axes of reception beams in the embodiment shown in FIGS. 15, 17, and 18.

The second interval means a void interval. The void interval is set to be longer than the first interval. Typically, the void interval has a width corresponding to two reception beams, as shown in FIGS. 4 and 5. In other words, the void interval is equal to the interval between the central axes of reception beams, of three adjacent reception beams spatially continuous along the scanning direction, which are located at the two ends. For example, a void corresponding to two reception beams is provided between the reception beams RB respectively indicated by "a" and "b", of the PSP beam group, which are located at an end portion. Likewise, a void corresponding to two reception beams is provided between the reception beams respectively indicated by "g" and "h". As described above, of the PSP beam group, the reception beams ("a" and "h") at the two ends are respectively shifted outside from the adjacent reception beams ("b" and "g") by one reception beam along the scanning direction. The void interval is not limited to two reception beams, and can be set to an arbitrary value equal to or more than a value corresponding to two reception beams. The void positions are not limited to the end portions of the PSP beam group (between "a" and "b" and between "g" and "h"), and may be provided at arbitrary positions in the PSP beam group.

The scanning scheme in which one void interval is provided at each of the two end portions of a PSP beam group will be referred to as "arrangement of one void at each end".

The scanning control unit 13 arbitrarily sets a void interval and a void position. The scanning control unit 13 arbitrarily sets the intervals between the central axes of reception beams other than the void intervals to the first interval. The scanning control unit 13 arbitrarily sets the first interval and the first interval position.

PSP of PSP beam groups by the reception unit 17 will be described next.

As shown in FIGS. 4 and 5, the reception unit 17 sequentially generates reception beam data sets for each PSP beam group along the scanning direction. First of all, in the first transmission, the transmission unit 15 transmits a transmission beam whose central axis is located in the middle between "1$d$" and "1$e$". The reception unit 17 receives a PSP beam group based on echo signals originating from reflected ultrasonic waves. The central axis of the PSP beam group PR1 is set to a position P1 like the central axis of the transmission beam. At the first transmission, the reception unit 17 receives eight reception beams indicated by "1$a$", "1$b$", "1$c$", "1$d$", "1$e$", "1$f$", "1$g$", and "1$h$". The reception unit 17 does not receive reception beams at the positions indicated by "void".

More specifically, the reception unit 17 generates a reception beam data set associated with "1$a$" based on echo signals from a plurality of transducers belonging to the reception opening corresponding to the reception position of "1$a$". The reception unit 17 then generates a reception beam data set associated with "1$b$" based on echo signals from a plurality of transducers belonging to the reception opening corresponding to the reception position of "1$b$" adjacent to "1$a$". The reception position of "1$a$" is adjacent to the reception position of "1$b$" through a void corresponding to two reception beams. The reception unit 17 generates a reception beam data set associated with "1$c$" based on a plurality of echo signals belonging to the reception opening corresponding to the reception position of "1$c$" adjacent to "1$b$". No void corresponding to one reception beam is provided between the reception position of "1$b$" and the reception position of "1$c$". In this manner, the reception unit 17 generates eight reception beam data sets at the positions "1$a$", "1$b$", "1$c$", "1$d$", "1$e$", "1$f$", "1$g$", and "1$h$". This generates a PSP beam data set group associated with the first transmission/reception.

After the first transmission/reception, the second transmission/reception is performed. In the second transmission, the transmission unit 15 transmits a transmission beam whose central axis is located in the middle between "2$d$" and "2$e$". In the same manner as in the first transmission/reception, the reception unit 17 receives eight reception beams indicated by "2$a$", "2$b$", "2$c$", "2$d$", "2$e$", "2$f$", "2$g$", and "2$h$". The central axis of the second transmission beam is spatially shifted from the central axis of the first transmission beam by two reception beams along the scanning direction. Therefore, likewise, the central axis of the second PSP beam group is also spatially shifted from the first PSP beam group by two reception beams along the scanning direction.

Note that the reception position of "1$h$" is set to be spatially the same position as the reception position of "2$g$". The reception position of "1$g$" is not at spatially the same position as the reception position of "2$f$", but is at spatially the same position as the reception position of "2$e$".

In this manner, the reception unit 17 generates all PSP beam groups for the formation of one scanning plane while shifting the PSP beam groups by two reception beams at a time in the scanning direction. In other words, the scanning control unit 13 sets the positions of a plurality of PSP beam groups so as to shift them from each other by two reception beams along the scanning direction.

Synthesizing of reception beam data sets by the synthesizing unit 19 will be described next with reference to FIG. 5. Assume that the reception beam data sets generated by the reception unit 17 are instantly stored in the reception beam storage unit 18.

In synthesizing processing, the synthesizing unit 19 generates a plurality of synthetic beam data sets respectively corresponding to a plurality of synthetic beams based on a plurality of PSP beam data set groups. More specifically, the synthesizing unit 19 reads out reception beam data sets to be synthesized from the reception beam storage unit 18, and synthesizes the readout reception beam data sets. The data sets to be synthesized are reception beam data sets associated with the reception position where a predetermined number of reception beam data sets are completely acquired. The number of reception beams to be synthesized is determined in accordance with, for example, the number of PSP beams and the number of beams to be shifted. This is because the maximum number of reception beams at one spatial position is uniquely determined in accordance with the number of PSP beams and the number of beams to be shifted. If, for example, the number of PSP beams is eight and the number of beams to be shifted is two, up to four reception beams are received at one spatial position. In this case, therefore, the number of reception beams to be synthesized is set to four. In this manner, the synthesizing unit 19 synthesizes a predetermined number of reception beams, of a plurality of reception beams, which are associated with the same reception position to generate a synthetic beam. In other words, the synthesizing unit 19 synthesizes a predetermined number of reception beam data sets associated with the same reception position to generate a synthetic beam data set corresponding to a synthetic beam.

More specifically, when four reception beams at the same reception position are acquired, the synthesizing unit 19 synthesizes the four reception beams. For example, the synthesizing unit 19 generates four reception beam data sets of "2$f$", "3$d$", "4$b$", and "5$a$" at a reception position PA. When the fourth reception beam data set of "5$a$" is generated, the synthesizing unit 19 synthesizes the four reception beam data sets of "2$f$", "3$d$", "4$b$", and "5$a$" to generate a synthetic beam data set O1 associated with the reception position PA. The synthesizing unit 19 generates four reception beam data sets of "1$h$", "2$g$", "3$e$", and "4$c$" at a reception position PB. When the fourth reception beam data set of "4$c$" is generated, the synthesizing unit 19 generates a synthetic beam data set O2 associated with the reception position PB based on the four reception beam data sets of "1h", "2g", "3e", and "4c". The synthetic beam storage unit 20 stores the generated synthetic beam data sets.

Figure 18:
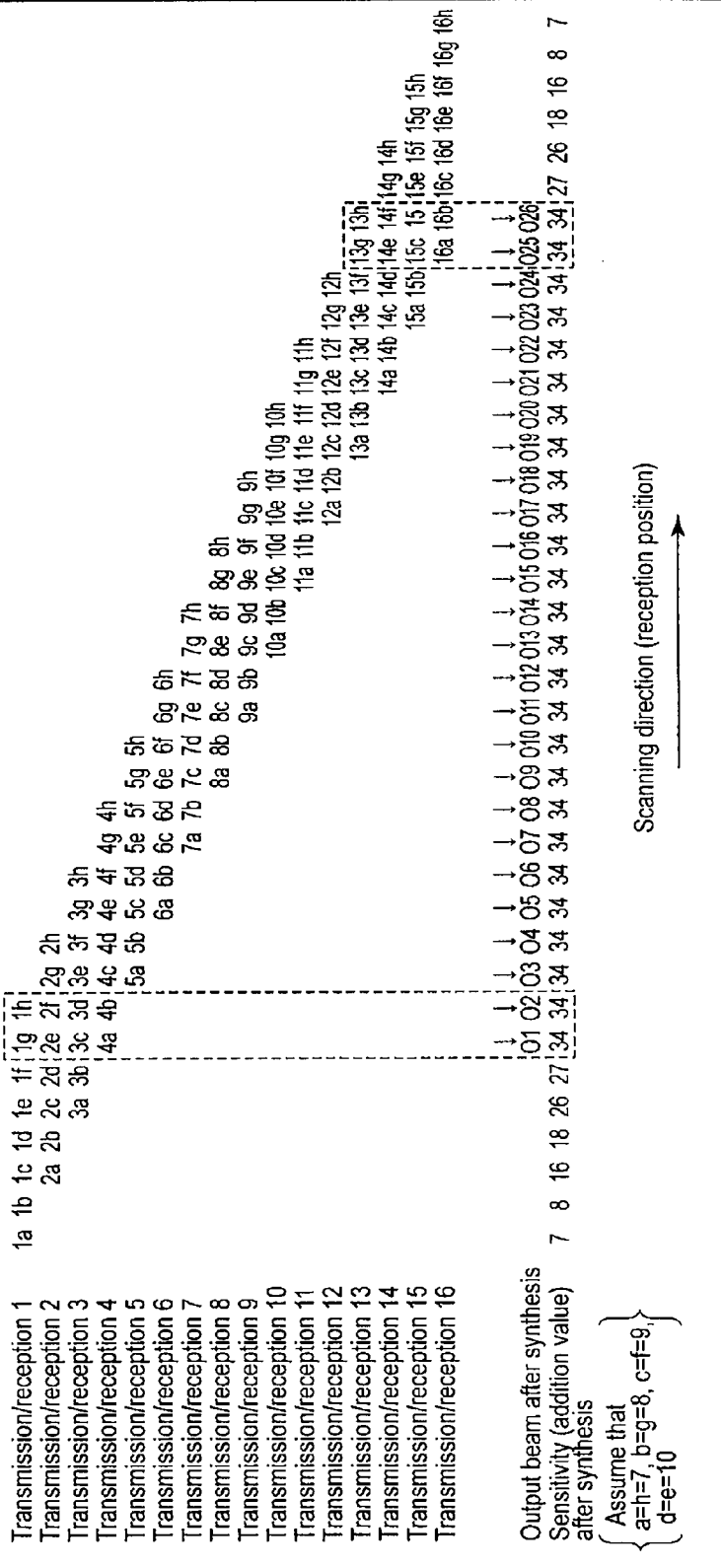
FIG. 18 is a view for explaining still another scanning scheme for PSP (parallel signal processing of eight beams & four-beam synthesis & two-beam shifting).

As shown in FIG. 5, "1a" and "1h" are set at positions located farther from the central axis of the PSP beam group than "1a" and "1h" in FIG. 18. Therefore, the reception sensitivity of the reception beam of "1a" in FIG. 5 is lower than that of the reception beam of "1a" in FIG. 18. It is, however, possible to neglect such a deterioration in reception sensitivity by synthesizing processing, as will be described later.

Note that at the two end portions of a scanning plane such as reception positions PO, not all four reception beam data sets are acquired. If only less than four reception beam data sets are acquired, the image generation unit 21 does not use the synthetic beam data set associated with the corresponding reception position for the generation of an image. Alternatively, if only less than four reception beam data sets are acquired, the synthesizing unit 19 need not generate any synthetic beam data set associated with the corresponding reception position. Conversely, if four reception beam data sets are acquired, the image generation unit 21 uses a synthetic beam data set associated with the corresponding reception position for the generation of an image.

Four reception beam data sets are acquired near the two end portions of a scanning plane like reception positions PO1. However, all four reception beam data sets are not acquired at a reception position PO2 located more inwardly than the reception position PO1 by one reception beam. The image generation unit 21 does not use a synthetic beam data set associated with the reception position PO2 between the reception position PO and the reception position PO1. Alternatively, the synthesizing unit 19 does not generate such data sets. In other words, the image generation unit 21 does not use, for the generation of an image, synthetic beam data sets associated with reception positions PO and PO1 located nearer to the end side of the scanning plane than the reception position PO2, at which not all four reception beam data sets are acquired, or the synthesizing unit 19 does not generate such data sets.

That is, a synthetic beam data set used for the generation of an image is that belonging to a spatial range in which four reception beam data sets are spatially and continuously acquired. A synthetic beam data set belonging to such a spatial range is supplied to the image generation unit 21. As described above, any synthetic beam data sets belonging to other than this spatial range are not used for the generation of an image by the image generation unit 21 or are not generated by the synthesizing unit 19.

For example, the image generation unit 21 reads out a synthetic beam data set used for the generation of an image from the synthetic beam storage unit 20, and uses the readout synthetic beam data set for the generation of an image. On the other hand, the image generation unit 21 does not read out any synthetic beam data set which is not used for the generation of an image from the synthetic beam storage unit 20. In image generation processing, the image generation unit 21 generates ultrasonic image data based on a plurality of readout synthetic beam data sets. More specifically, the image generation unit 21 arranges the readout synthetic beam data sets in the image memory in the image generation unit 21 in accordance with output times. This arrangement processing will generate ultrasonic image data which can be displayed on the display unit 25.

Note that the output order and spatial arrangement of synthetic beam data sets are reversed in some cases. For example, the synthetic beam data set O2 associated with the reception position PB is output at the fourth transmission/reception. On the other hand, the synthetic beam O1 associated with the reception position PA located before the reception position PB in the scanning direction (i.e., earlier reception time) is output at the fifth transmission/reception. When ultrasonic image data is generated while the output order and spatial arrangement of synthetic beams are reversed, the scanning lines associated with two synthetic beam data sets in the generated ultrasonic image data are reversed on an image. The image generation unit 21 therefore rearranges the synthetic beam data sets, whose output order and spatial arrangement are reversed, in accordance with the reception position so as to match the output order and the spatial arrangement. For example, the image generation unit 21 sequentially arrays synthetic beam data sets at storage addresses in accordance with the reception position. Alternatively, the image generation unit 21 rearranges the storage addresses of the synthetic beam data sets in the synthetic beam storage unit 20 in accordance with the reception position. Alternatively, it is possible to rearrange the output order of synthetic beam data sets from the synthesizing unit 19 so as to sequentially output the data sets along the scanning direction.

In the above description, any synthetic beam data set based on less than four reception beam data sets is not used for the generation of an image. However, this embodiment is not limited to this. The image generation unit 21 may use a synthetic beam data set based on less than four reception beam data sets for the generation of an image. For example, the synthesizing unit 19 may generate a synthetic beam data set at a missing reception position from reception beam data sets at surrounding non-missing reception positions by interpolation. Note that a missing reception position is a reception position where not all four reception beams are acquired, and a non-missing reception position is a reception position where all four reception beams are acquired. Surrounding non-mission reception positions are, for example, reception positions adjacent to each other through the reception position PO2. A reception beam data set generated by interpolation will be referred to as an interpolated beam data set. The interpolated beam data set is stored in the synthetic beam storage unit 20. The image generation unit 21 can read out an interpolated beam data set from the synthetic beam storage unit 20 and use it for the generation of an image.

To explain the image quality of an ultrasonic image here, pseudo sensitivity is set for each reception beam. Assume that the sensitivities of reception beams linearly decrease with the distance from the central axis of the PSP beam group. More specifically, assume that the sensitivities of reception beams of "a" and "h" are "6", the sensitivities of reception beams of "b" and "g" are "8", the sensitivities of reception beams of "c" and "f" are "9", and the sensitivities of reception beams of "d" and "e" are "10".

In this case, all the synthetic beams used for the generation of an image have the same sensitivity "33". Therefore, an ultrasonic image undergoes no deterioration in image quality due to reception sensitivity unevenness of reception beams.

In this embodiment, the number of beams to be shifted is set to a plurality of reception beams (two in the case shown in FIG. 5). In the embodiment, therefore, it is possible to generate ultrasonic image data by synthesizing reception beams smaller in number than the number of PSP beams. With this operation, the embodiment increases the frame rate as compared with the case shown in FIG. 17 in which reception beams equal in number to the number of PSP beams are synthesized.

In this embodiment, a plurality of reception beams included in a PSP beam group are arranged at unequal intervals. In the embodiment, therefore, the phases of synthetic beams switch for each synthetic beam. The embodiment can therefore reduce a deterioration in the image quality of ultrasonic image data as compared with the case shown in FIG. 18 in which the phases of synthetic beams switch for each set of a plurality of synthetic beams (more specifically, two synthetic beams).

With these effects, the ultrasonic diagnostic apparatus and ultrasonic transmission/reception method according to this embodiment can generate ultrasonic image data with high image quality concerning even a fast moving region such as the heart while maintaining real-time performance with a high frame rate. The ultrasonic diagnostic apparatus and ultrasonic transmission/reception method according to the present invention can therefore improve the diagnosis performance in ultrasonic examination.

This embodiment can therefore provide an ultrasonic diagnostic apparatus and ultrasonic transmission/reception method which can simultaneously increase the frame rate and improve image quality in PSP.

Figure 8:
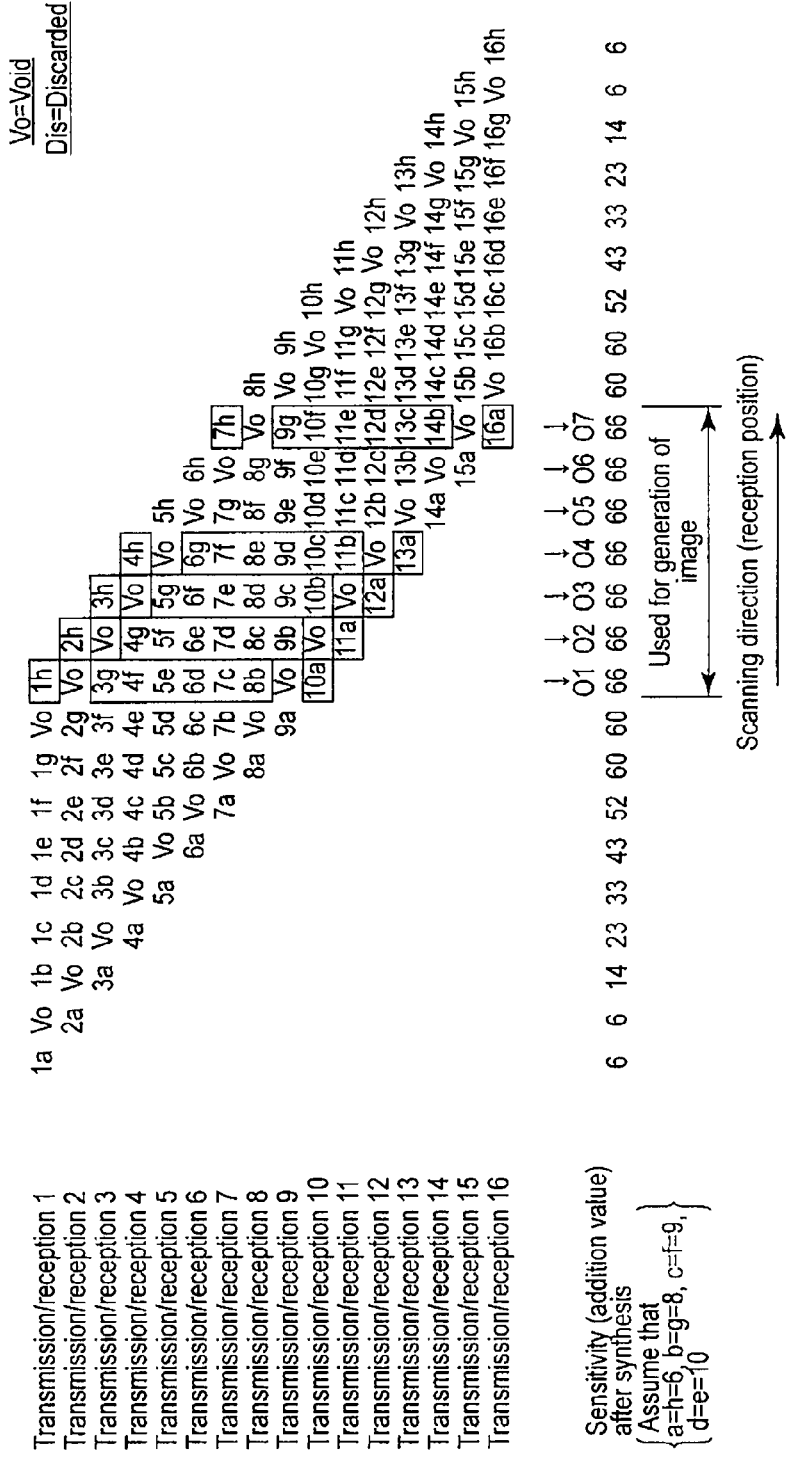
FIG. 8 is a view for explaining a scanning scheme (parallel signal processing of eight beams & eight-beam synthesis & one-beam shifting & arrangement of one void at each end) according to the third modification of this embodiment.

Note that the scanning scheme according to this embodiment is not limited to only (parallel signal processing of eight beams & four-beam synthesis & two-beam shifting & arrangement of one void at each end) shown in FIGS. 5 and 8. Other scanning schemes according to this embodiment will be described below in a plurality of modifications. Note that the same reference numerals in the following description denote constituent elements having almost the same functions and arrangements as in the embodiment, and a repetitive description will be made only when required.

(First Modification)

Figure 6:
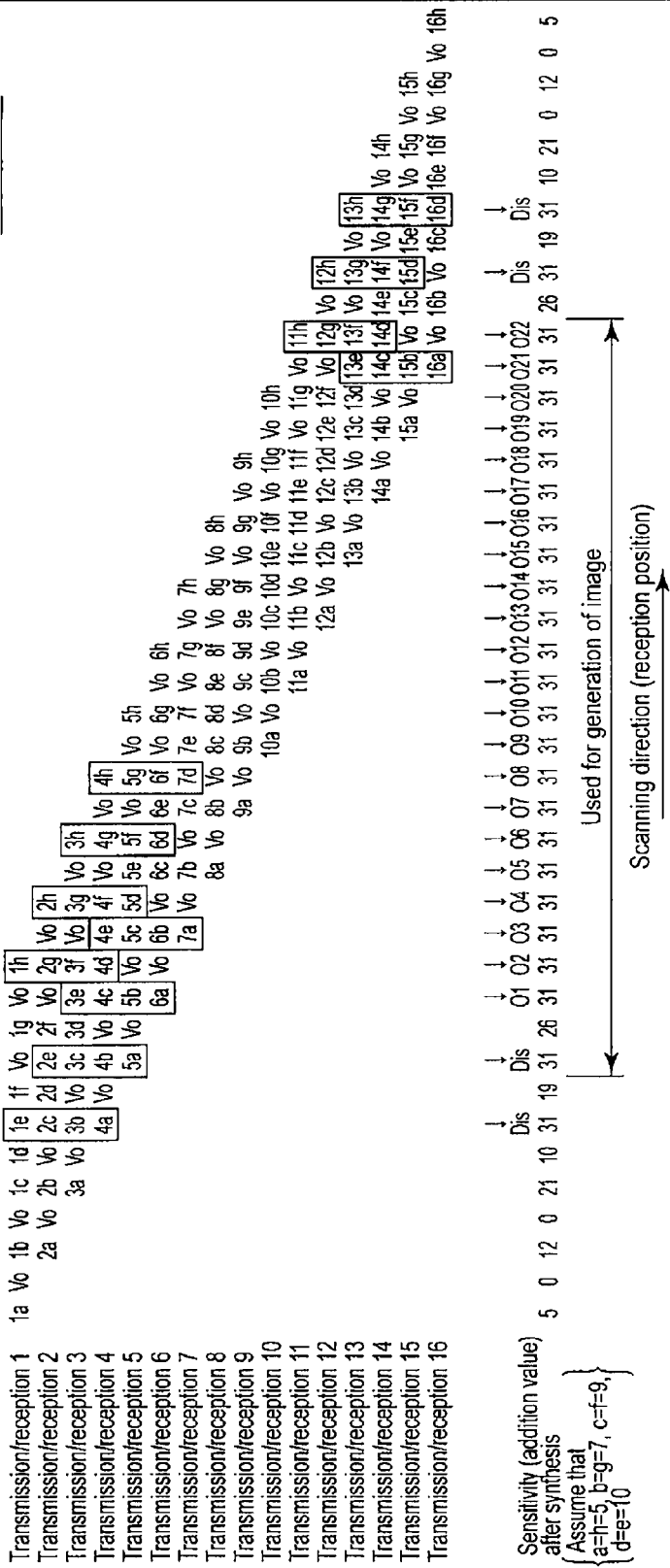
FIG. 6 is a view for explaining a scanning scheme (parallel signal processing of eight beams & four-beam synthesis & two-beam shifting & arrangement of two discrete voids at each end) according to the first modification of this embodiment.

FIG. 6 is a view for explaining a scanning scheme according to the first modification. As shown in FIG. 6, the scanning scheme according to the first modification is (parallel signal processing of eight beams & four-beam synthesis & two-beam shifting & arrangement of two discrete voids at each end). In the "arrangement of two discrete voids at each end", two voids are discretely arranged at each of the two end portions of a PSP beam group. More specifically, the scanning control unit 13 sets the following intervals to an interval corresponding to two reception beams: the interval between reception positions "a" and "b", the interval between reception positions "b" and "c", the interval between reception positions "f" and "g", and the interval between reception positions "g" and "h", which are located at the end portions of the PSP beam group. On the other hand, the scanning control unit 13 sets the following intervals to an interval corresponding to one reception beam: the interval between reception positions "c" and "d", the interval between reception positions "d" and "e", and the interval between reception positions "e" and "f", located at the middle portion of the PSP beam group.

In the scanning scheme according to the first modification, all the synthetic beams used for the generation of an image have the same sensitivity "31". Therefore, the ultrasonic image generated by the scanning scheme according to the first modification undergoes no deterioration in image quality due to reception sensitivity unevenness of reception beams.

In the scanning scheme according to the first modification, the number of beams to be shifted is set to two. The ultrasonic diagnostic apparatus according to the first modification can therefore generate ultrasonic image data by synthesizing a smaller number of reception beams than the number of PSP beams. With this operation, the scanning scheme according to the first modification can increase the frame rate as compared with the scanning scheme in FIG. 17.

In the scanning scheme according to the first modification, a plurality of reception beams included in a PSP beam group are arranged at unequal intervals. Therefore, the phases of synthetic beams switch for each synthetic beam. The scanning scheme according to the first modification can therefore reduce a deterioration in the image quality of ultrasonic image data as compared with the scanning scheme in FIG. 18.

As is obvious from the comparison between FIGS. 6 and 5, "arrangement of one void at each end" can use a larger number of synthetic beams for the generation of an image than "arrangement of two discrete voids at each end" when the number of times of transmission/reception remains the same. Therefore, "arrangement of one void at each end" can obtain ultrasonic image data in a wider range than in "arrangement of two discrete voids at each end".

As is obvious from the comparison between FIGS. 6 and 5, "arrangement of one void at each end" obtains a synthetic beam with higher sensitivity than that obtained by "arrangement of two discrete voids at each end". Therefore, "arrangement of one void at each end" can obtain ultrasonic image data with higher image quality than that obtained by "arrangement of two discrete voids at each end"

(Second Modification)

Figure 7:
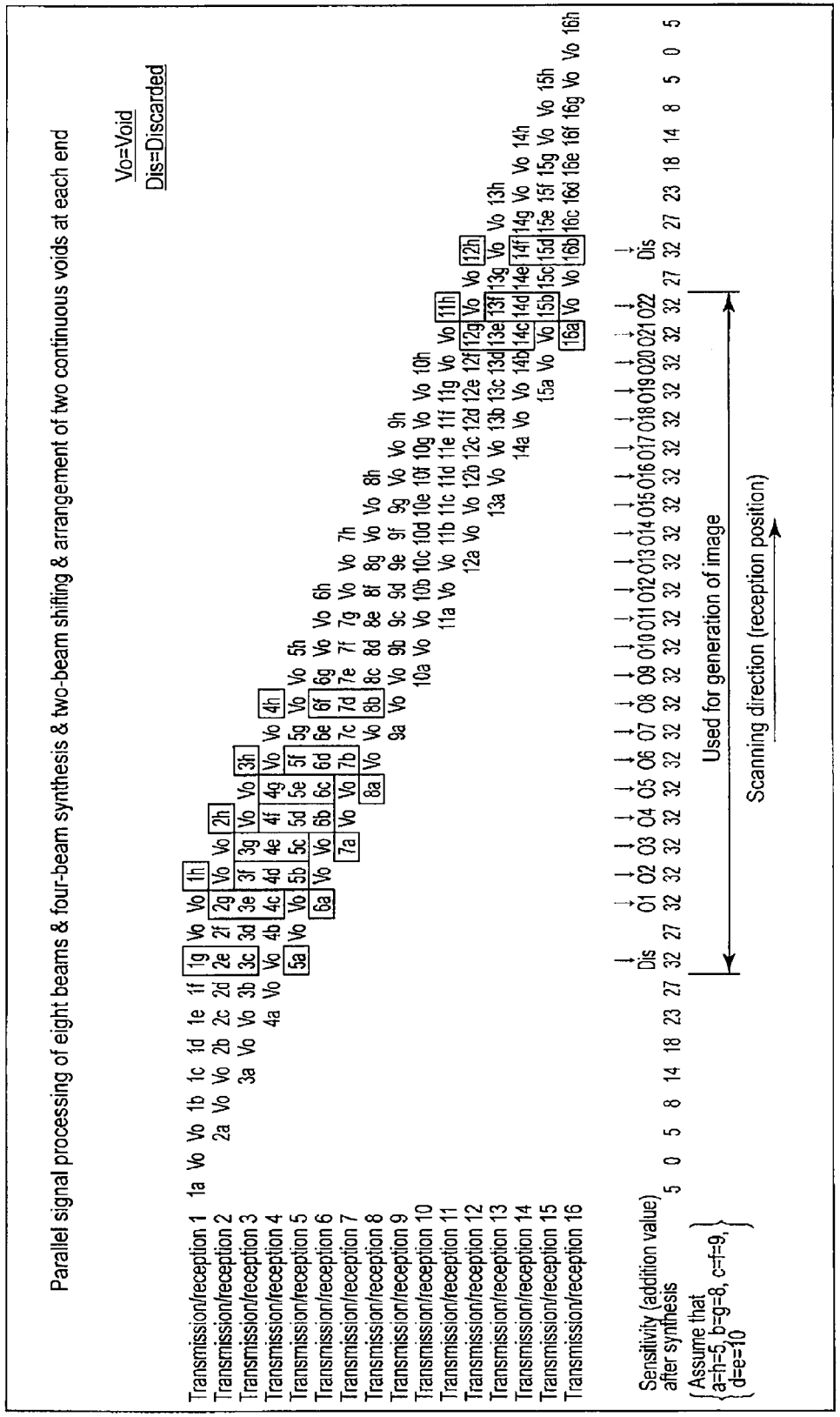
FIG. 7 is a view for explaining a scanning scheme (parallel signal processing of eight beams & four-beam synthesis & two-beam shifting & arrangement of two continuous voids at each end) according to the second modification of this embodiment.

FIG. 7 is a view for explaining a scanning scheme according to the second modification. As shown in FIG. 7, the scanning scheme according to the second modification is (simultaneous reception of eight beams & four-beam synthesis & two-beam shifting & arrangement of two continuous voids at each end). In "arrangement of two continuous voids at each end", two voids are continuously arranged at each end portion of a PSP beam group. In other words, in "arrangement of two continuous voids at each end", a void corresponding to the interval of two voids is placed at each end portion of a PSP beam group. More specifically, the scanning control unit 13 sets the following intervals to an interval corresponding to four reception beams: the interval between reception position "a" and reception position "b" and the interval between reception position "g" and reception position "h", which are located at the end portions of the PSP beam group. On the other hand, the scanning control unit 13 sets the following intervals to an interval corresponding to one reception beam: the interval between reception position "b" and reception position "c", the interval between reception position "c" and reception position "d", the interval between reception position "d" and reception position "e", the interval between reception position "e" and reception position "f", and the interval between reception position "f" and reception position "g", which are located at the middle portion of the PSP beam group.

In the scanning scheme according to the second modification, all the synthetic beams used for the generation of an image have the same sensitivity "32". Therefore, the ultrasonic image generated by the scanning scheme according to the second modification undergoes no deterioration in image quality due to reception sensitivity unevenness of reception beams.

In the scanning scheme according to the second modification, the number of beams to be shifted is set to two. The ultrasonic diagnostic apparatus according to the second modification can therefore generate ultrasonic image data by synthesizing a smaller number of reception beams than the number of PSP beams. With this operation, the ultrasonic diagnostic apparatus according to the second modification can increase the frame rate as compared with the scanning scheme in FIG. 17.

In the scanning scheme according to the second modification, a plurality of reception beams included in a PSP beam group are arranged at unequal intervals. That is, the phases of synthetic beams switch for each synthetic beam. The ultrasonic diagnostic apparatus according to the second modification can therefore reduce a deterioration in the image quality of ultrasonic image data as compared with the scanning scheme in FIG. 18.

As is obvious from the comparison between FIGS. 7 and 5, "arrangement of one void at each end" can use a larger number of synthetic beams for the generation of an image than "arrangement of two continuous voids at each end" when the number of times of transmission/reception remains the same. Therefore, "arrangement of one void at each end" can obtain ultrasonic image data in a wider range than in "arrangement of two continuous voids at each end". As is obvious from FIGS. 7 and 6, "arrangement of two continuous voids at each end" can use the same number of synthetic beams for the generation of an image as that in "arrangement of two discrete voids at each end" when the number of times of transmission/reception remains the same. Therefore, "arrangement of two continuous voids at each end" can obtain ultrasonic image data in almost the same range as that obtained by "arrangement of two discrete voids at each end".

As is obvious from the comparison between FIGS. 7 and 5, "arrangement of one void at each end" obtains a synthetic beam with higher sensitivity than that obtained by "arrangement of two continuous voids at each end". Therefore, "arrangement of one void at each end" can obtain ultrasonic image data with higher image quality than that obtained by "arrangement of two continuous voids at each end". As is also obvious from the comparison between FIGS. 7 and 6, "arrangement of two continuous voids at each end" obtains a synthetic beam with higher sensitivity than that obtained by "arrangement of two discrete voids at each end". Therefore, "arrangement of two continuous voids at each end" can obtain ultrasonic image data with higher image quality than that obtained by "arrangement of two discrete voids at each end".

(Third Modification)

FIG. 8 is a view for explaining a scanning scheme according to the third modification. As shown in FIG. 8, the scanning scheme according to the third modification is (parallel signal processing of eight beams & eight-beam synthesis & one-beam shifting & arrangement of one void at each end). More specifically, the scanning control unit 13 sets the following intervals to an interval corresponding to four reception beams: the interval between reception position "a" and reception position "b" and the interval between reception position "g" and reception position "h", which are located at the end portions of the PSP beam group. On the other hand, the scanning control unit 13 sets the following intervals to an interval corresponding to one reception beam: the interval between reception position "b" and reception position "c", the interval between reception position "c" and reception position "d", the interval between reception position "d" and reception position "e", the interval between reception position "e" and reception position "f", and the interval between reception position "f" and reception position "g", which are located at the middle portion of the PSP beam group. Note that in "eight-beam synthesis", a synthetic beam is formed at each reception position where eight reception beams are acquired.

In the scanning scheme according to the third modification, all the synthetic beams used for the generation of an image have the same sensitivity "66". Therefore, the ultrasonic image generated by the scanning scheme according to the third modification undergoes no deterioration in image quality due to reception sensitivity unevenness of reception beams.

In the scanning scheme according to the third modification, a plurality of reception beams included in a PSP beam group are arranged at unequal intervals. That is, the phases of synthetic beams switch for each synthetic beam. The ultrasonic diagnostic apparatus according to the third modification can therefore reduce a deterioration in the image quality of ultrasonic image data as compared with the scanning scheme in FIG. 18.

As is obvious from the comparison between FIGS. 8 and 5, "two-beam shifting" can use a larger number of synthetic beams for the generation of an image than "one-beam shifting" when the number of times of transmission/reception remains the same. Therefore, "two-beam shifting" can obtain ultrasonic image data in a wider range than in "one-beam shifting".

As is obvious from the comparison between FIGS. 8 and 5, "four-beam synthesis" uses a smaller number of reception beams for the generation of one synthetic beam than "eight-beam synthesis". Therefore, "four-beam synthesis" can generate ultrasonic image data in a shorter time than "eight-beam synthesis", and hence is superior to "eight-beam synthesis" in terms of the real-time performance of ultrasonic image data. Accordingly, "four-beam synthesis" is higher in visualization ability than "eight-beam synthesis" with respect to a moving object such as the heart.

(Fourth Modification)

Figure 9:
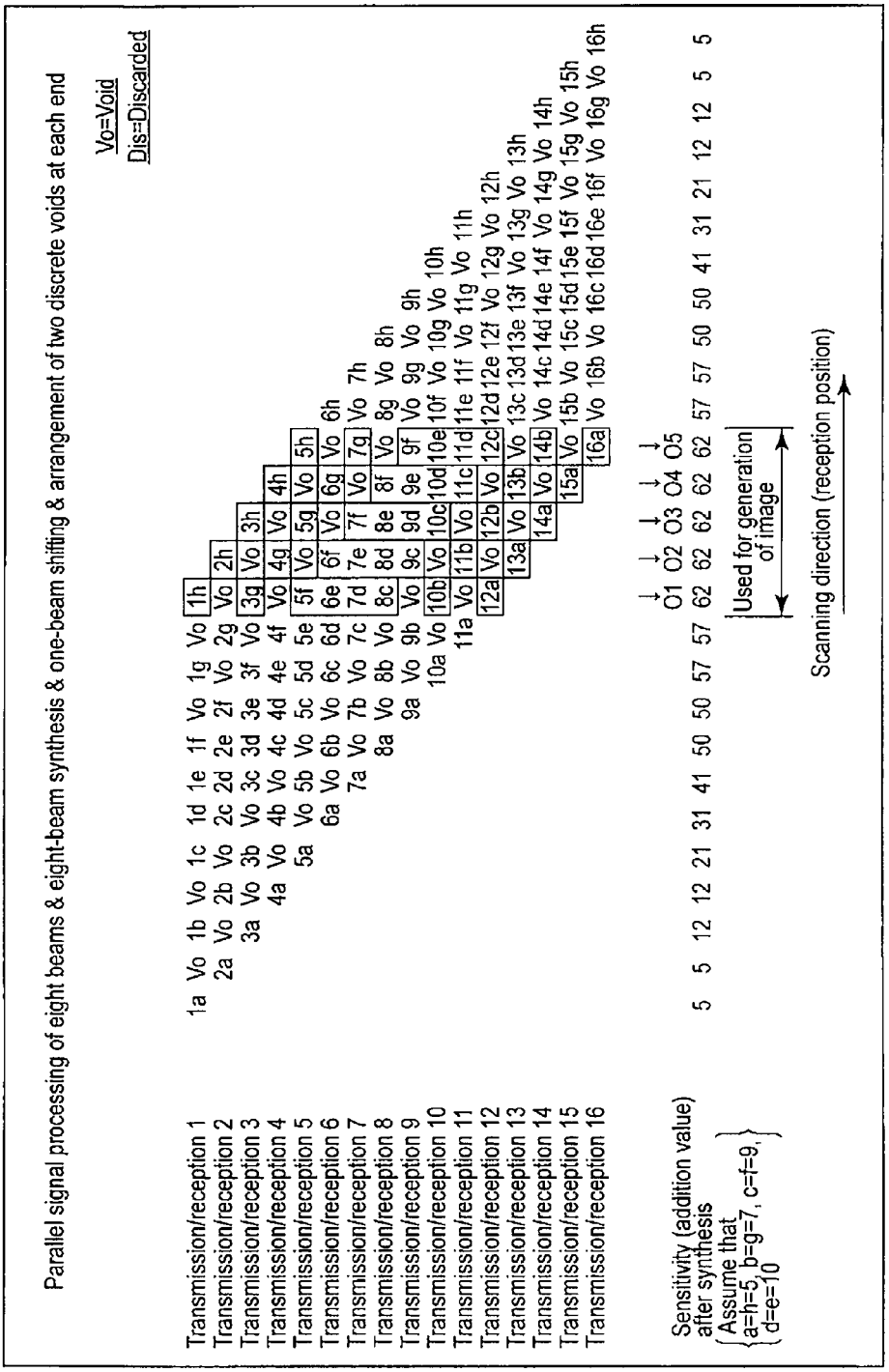
FIG. 9 is a view for explaining a scanning scheme (parallel signal processing of eight beams & eight-beam synthesis & one-beam shifting & arrangement of two discrete voids at each end) according to the fourth modification of this embodiment.

FIG. 9 is a view for explaining a scanning scheme according to the fourth modification. As shown in FIG. 9, the scanning scheme according to the fourth modification is (parallel signal processing of eight beams & eight-beam synthesis & one-beam shifting & arrangement of two discrete voids at each end). More specifically, the scanning control unit 13 sets the following intervals to an interval corresponding to two reception beams: the interval between reception position "a" and reception position "b", the interval between reception position "b" and reception position "c", the interval between reception position "f" and reception position "g", and the interval between reception position "g" and reception position "h", which are located at the end portions of the PSP beam group. On the other hand, the scanning control unit 13 sets the following intervals to an interval corresponding to one reception beam: the interval between reception position "c" and reception position "d", the interval between reception position "d" and reception position "e", and the interval between reception position "e" and reception position "f", which are located at the middle portion of the PSP beam group.

In the scanning scheme according to the fourth modification, all the synthetic beams used for the generation of an image have the same sensitivity "62". Therefore, the ultrasonic image generated by the scanning scheme according to the fourth modification undergoes no deterioration in image quality due to reception sensitivity unevenness of reception beams.

In the scanning scheme according to the fourth modification, a plurality of reception beams included in a PSP beam group are arranged at unequal intervals. That is, the phases of synthetic beams switch for each synthetic beam. The ultrasonic diagnostic apparatus according to the fourth modification can therefore reduce a deterioration in the image quality of ultrasonic image data as compared with the scanning scheme in FIG. 18.

As is obvious from the comparison between FIGS. 9 and 8, in "arrangement of one void at each end", "eight-beam synthesis & one-beam shifting" is smaller in the number of times of transmission/reception necessary for the formation of one synthetic beam than "arrangement of two discrete voids at each end". In "arrangement of one void at each end", "eight-beam synthesis & one-beam shifting" exhibits better real-time performance than "arrangement of two discrete voids at each end".

(Fifth Modification)

Figure 10:
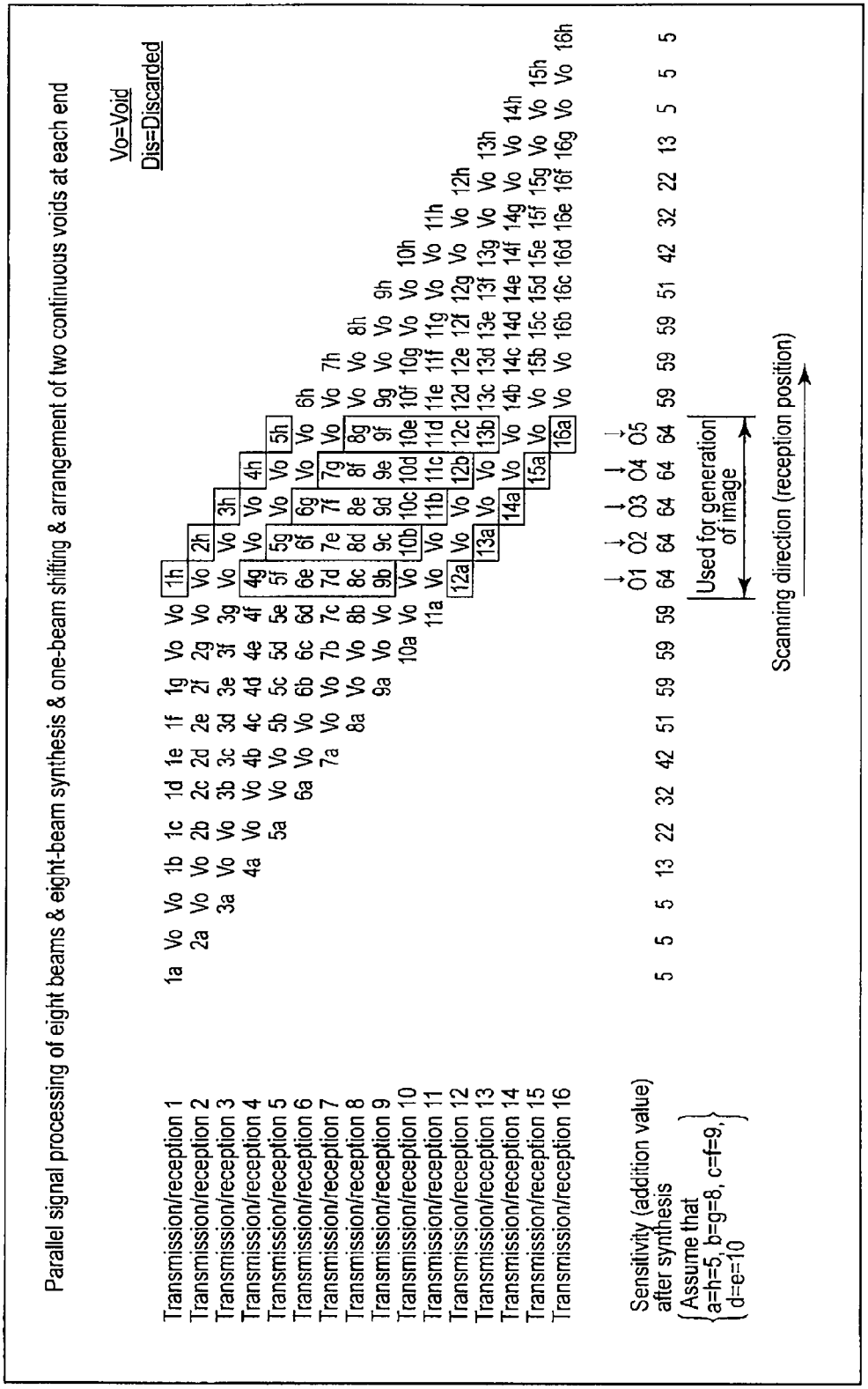
FIG. 10 is a view for explaining a scanning scheme (parallel signal processing of eight beams & eight-beam synthesis & one-beam shifting & arrangement of two continuous voids at each end) according to the fifth modification of this embodiment.
Figure 12:
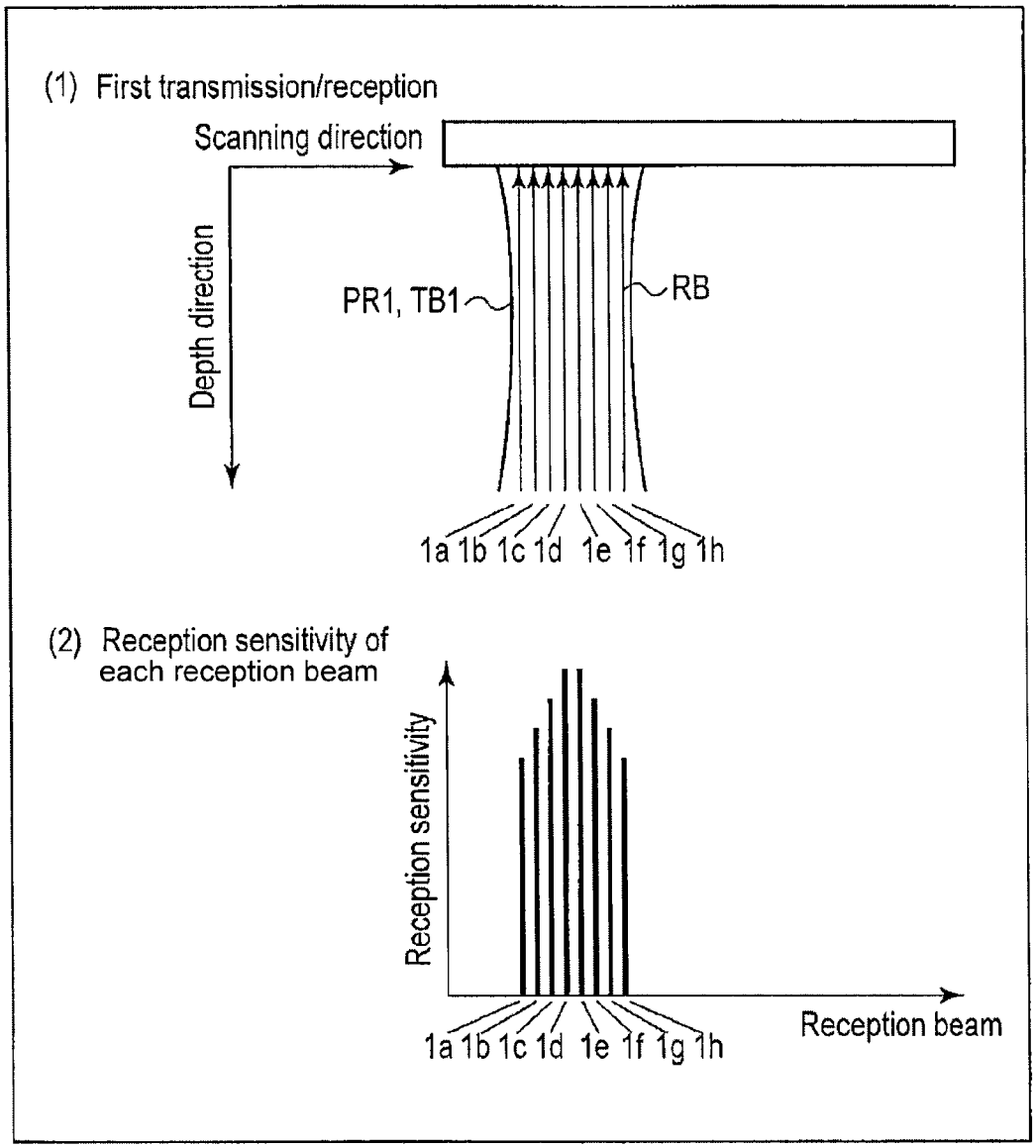
FIG. 12 is a view for explaining reception sensitivity nonuniformity in the scanning scheme in FIG. 11.
Figure 13:
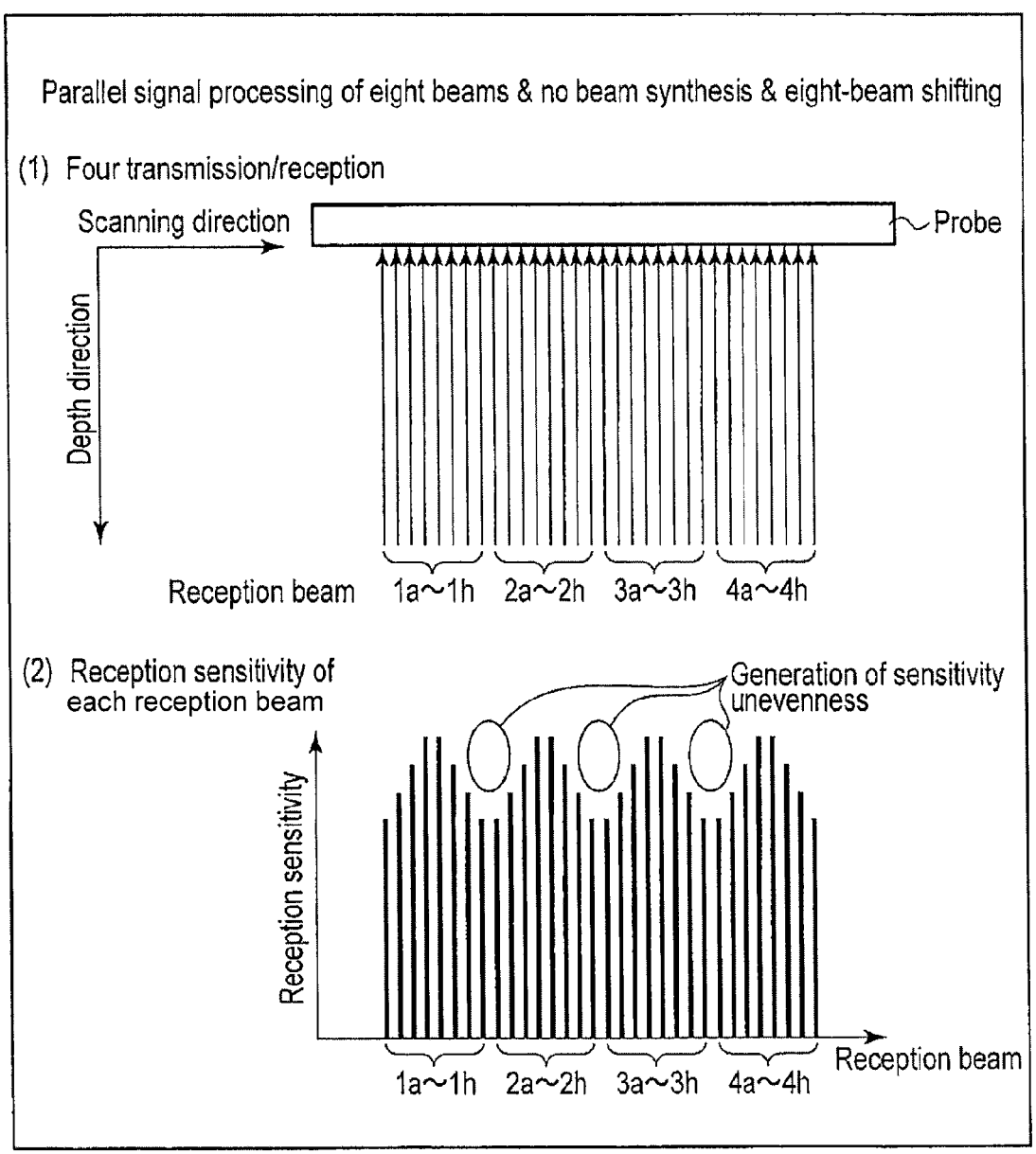
FIG. 13 is another view for explaining reception sensitivity nonuniformity in the scanning scheme in FIG. 11.
Figure 14:
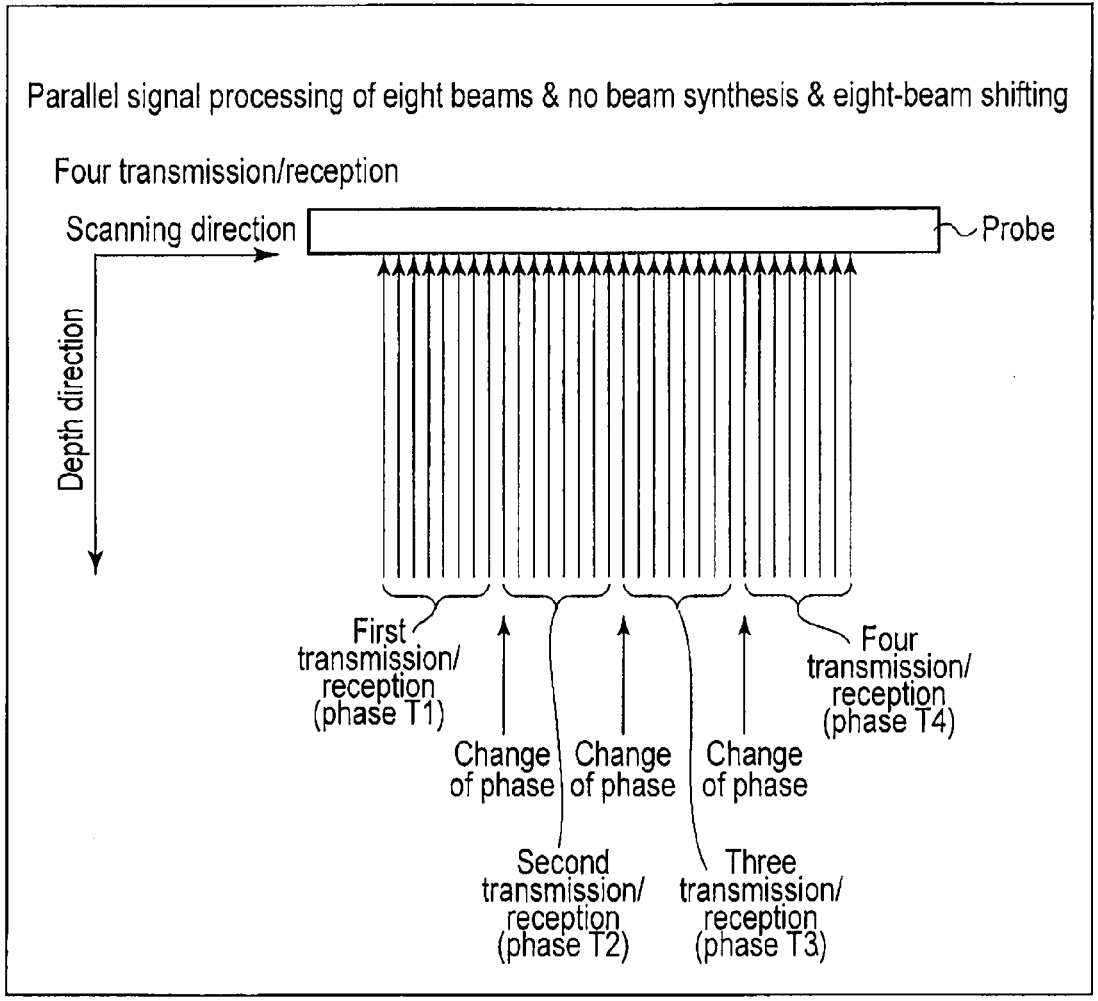
FIG. 14 is a view for explaining the phase differences between PSP beam groups in the scanning scheme in FIG. 11.

FIG. 10 is a view for explaining a scanning scheme according to the fifth modification. As shown in FIG. 10, the scanning scheme according to the fifth modification is (parallel signal processing of eight beams & eight-beam synthesis & one-beam shifting & arrangement of two continuous voids at each end). More specifically, the scanning control unit 13 sets the following intervals to an interval corresponding to four reception beams: the interval between reception position "a" and reception position "b" and the interval between reception position "g" and reception position "h", which are located at the end portions of the PSP beam group. On the other hand, the scanning control unit 13 sets the following intervals to an interval corresponding to one reception beam: the interval between reception position "b" and reception position "c", the interval between reception position "c" and reception position "d", the interval between reception position "d" and reception position "e", the interval between reception position "e" and reception position "f", and the interval between reception position "f" and reception position "g", which are located at the middle portion of the PSP beam group.

In the scanning scheme according to the fifth modification, all the synthetic beams used for the generation of an image have the same sensitivity "64". Therefore, the ultrasonic image generated by the scanning scheme according to the fifth modification undergoes no deterioration in image quality due to reception sensitivity unevenness of reception beams.

In the scanning scheme according to the fifth modification, a plurality of reception beams included in a PSP beam group are arranged at unequal intervals. That is, the phases of synthetic beams switch for each synthetic beam. The ultrasonic diagnostic apparatus according to the fifth modification can therefore reduce a deterioration in the image quality of ultrasonic image data as compared with the scanning scheme in FIG. 18.

As is obvious from the comparison between FIGS. 10 and 8, in "arrangement of one void at each end", "eight-beam synthesis & one-beam shifting" is smaller in the number of times of transmission/reception necessary for the formation of one synthetic beam than "arrangement of two continuous voids at each end". In "arrangement of one void at each end", "eight-beam synthesis & one-beam shifting" exhibits better real-time performance than "arrangement of two continuous voids at each end". In addition, as is obvious from the comparison between FIGS. 10 and 9, in "arrangement of two continuous voids at each end", "eight-beam synthesis & one-beam shifting" is equal in the number of times of transmission/reception necessary for the formation of one synthetic beam to "arrangement of two discrete voids at each end". In "arrangement of two continuous voids at each of two ends", "eight-beam synthesis & one-beam shifting" exhibits almost the same real-time performance as "arrangement of two discrete voids at each end".

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus comprising:
    a probe including a plurality of transducers configured to repeatedly transmit transmission beams to a subject, repeatedly receive ultrasonic waves reflected by the subject, and repeatedly generate echo signals corresponding to the received ultrasonic waves;
    a reception unit configured to generate a plurality of reception beam data set groups based on the generated echo signals, each of the reception beam data set groups including a plurality of reception beam data sets respectively corresponding to a plurality of reception beams associated with parallel signal processing, and each of the reception beam data sets being generated based on echo signals from transducers, of the transducers, which are associated with a corresponding reception position;
    a control unit configured to set a spatial arrangement of the reception beams and arrange the reception beams at unequal intervals;
    a synthesizing unit configured to generate a plurality of synthetic beam data sets associated with a plurality of reception positions based on the reception beam data set groups, each of the synthetic beam data sets being obtained by synthesizing reception beam data sets, of the reception beam data sets included in the reception beam data set groups, which are associated with the same reception position; and
    a generation unit configured to generate ultrasonic image data associated with the subject based on the synthetic beam data sets.

2. The ultrasonic diagnostic apparatus of claim 1, wherein an interval between center positions of two adjacent reception beams of the reception beams includes a first interval and a second interval longer than the first interval.

3. The ultrasonic diagnostic apparatus of claim 2, wherein the control unit sets an interval between a center position of a reception beam, of the reception beams, which is located at an end, and a center position of a reception beam adjacent to the reception beam located at the end to the second interval, and sets an interval between center positions of other reception beams, of the reception beams, to the first interval.

4. The ultrasonic diagnostic apparatus of claim 1, wherein the control unit arranges the reception beam groups so as to shift the reception beam groups from each other by two reception beams along a scanning direction.

5. The ultrasonic diagnostic apparatus of claim 1, wherein the generation unit uses, for generation of an image, synthetic beam data sets associated with a first reception position, of the reception positions, at which a predetermined number of reception beam data sets are acquired, and
    neither the generation unit uses, for generation of an image, nor the synthesizing unit generates, reception beam data sets or synthetic beam data sets associated with a second reception position, of the reception positions, at which a predetermined number of reception beam data sets are acquired.

6. The ultrasonic diagnostic apparatus of claim 5, wherein neither the generation unit uses, for generation of an image, nor the synthesizing unit generates, synthetic beam data sets associated with a third reception position located nearer to an end side of a scanning plane than the second reception position.

7. The ultrasonic diagnostic apparatus of claim 5, wherein the synthesizing unit interpolates a synthetic data set associated with the second reception position based on reception data sets associated with reception positions around the second reception position.

8. The ultrasonic diagnostic apparatus of claim 1, wherein the generation unit rearranges the synthetic beam data sets output from the synthesizing unit in accordance with a reception position.

9. An ultrasonic transmission/reception method comprising:
repeatedly transmitting transmission beams to a subject;
repeatedly receiving ultrasonic waves reflected by the subject;
repeatedly generating echo signals corresponding to the received ultrasonic waves by using a probe;
generating a plurality of reception beam data set groups based on the generated echo signals, each of the reception beam data set groups including a plurality of reception beam data sets respectively corresponding to a plurality of reception beams associated with parallel signal processing, and each of the reception beam data sets being generated based on echo signals associated with a corresponding reception position;
setting a spatial arrangement of the reception beams and arranging the reception beams at unequal intervals;
generating a plurality of synthetic beam data sets associated with a plurality of reception positions based on the reception beam data set groups, each of the synthetic beam data sets being obtained by synthesizing reception beam data sets, of the reception beam data sets included in the reception beam data set groups, which are associated with the same reception position; and
generating ultrasonic image data associated with the subject based on the synthetic beam data sets.

10. The ultrasonic transmission/reception method of claim 9, wherein
an interval between center positions of two adjacent reception beams of the reception beams includes a first interval and a second interval longer than the first interval.

11. The ultrasonic transmission/reception method of claim 10, wherein
the setting comprises setting an interval between a center position of a reception beam, of the reception beams, which is located at an end, and a center position of a reception beam adjacent to the reception beam located at the end to the second interval, and setting an interval between center positions of other reception beams, of the reception beams, to the first interval.

12. The ultrasonic transmission/reception method of claim 9, wherein
the setting comprises arranging the reception beam groups so as to shift the reception beam groups from each other by two reception beams.

13. The ultrasonic transmission/reception method of claim 9, wherein
synthetic beam data sets associated with a first reception position, of the reception positions, at which a predetermined number of reception beam data sets are acquired are used for generation of an image in the generating, and
reception beam data sets or synthetic beam data sets associated with a second reception position, of the reception positions, at which a predetermined number of reception beam data sets are acquired are not used for generation of an image or are not generated in the synthesizing.

14. The ultrasonic transmission/reception method of claim 13, wherein synthetic beam data sets associated with a third reception position located nearer to an end side of a scanning plane than the second reception position are not used for generation of an image in the generating or are not generated in the synthesizing.

15. The ultrasonic transmission/reception method of claim 13, wherein
the synthesizing comprises interpolating a synthetic data set associated with the second reception position based on reception data sets associated with reception positions around the second reception position.

16. The ultrasonic transmission/reception method of claim 9, wherein
the generating comprises rearranging the synthetic beam data sets in accordance with a reception position.

* * * * *